United States Patent
Hawkett et al.

(10) Patent No.: US 8,852,641 B2
(45) Date of Patent: *Oct. 7, 2014

(54) POLYMER MICROGEL BEADS AND PREPARATIVE METHOD THEREOF

(75) Inventors: Brian Stanley Hawkett, Mona Vale (AU); Nirmesh Jain, Paramatta (AU)

(73) Assignee: The University of Sydney (AU)

(*) Notice: Subject to any disclaimer, the term of this patent is extended or adjusted under 35 U.S.C. 154(b) by 845 days.

This patent is subject to a terminal disclaimer.

(21) Appl. No.: 12/993,040

(22) PCT Filed: May 15, 2009

(86) PCT No.: PCT/AU2009/000618
§ 371 (c)(1),
(2), (4) Date: Feb. 3, 2011

(87) PCT Pub. No.: WO2009/137888
PCT Pub. Date: Nov. 19, 2009

(65) Prior Publication Data
US 2011/0118533 A1    May 19, 2011

(30) Foreign Application Priority Data
May 16, 2008  (AU) .................. 2008902430

(51) Int. Cl.
| | | |
|---|---|---|
| A61K 9/14 | (2006.01) | |
| C08F 4/00 | (2006.01) | |
| A61K 9/00 | (2006.01) | |
| C08F 2/38 | (2006.01) | |
| C08F 293/00 | (2006.01) | |
| C08F 220/56 | (2006.01) | |
| A61K 9/16 | (2006.01) | |
| C08F 2/44 | (2006.01) | |
| A61K 41/00 | (2006.01) | |
| C08F 2/32 | (2006.01) | |
| C08K 3/08 | (2006.01) | |
| C08K 3/22 | (2006.01) | |
| C08K 9/08 | (2006.01) | |

(52) U.S. Cl.
CPC ............... *A61K 9/0009* (2013.01); *C08K 3/08* (2013.01); *C08F 4/00* (2013.01); *C08K 3/22* (2013.01); *C08F 2/38* (2013.01); *A61K 9/0019* (2013.01); *C08K 9/08* (2013.01); *C08F 293/005* (2013.01); *C08F 220/56* (2013.01); *A61K 9/1611* (2013.01); *C08F 2/44* (2013.01); *A61K 41/0052* (2013.01); *A61K 9/1635* (2013.01); *C08F 2438/03* (2013.01); *C08F 2/32* (2013.01)
USPC ....................................... 424/489

(58) Field of Classification Search
None
See application file for complete search history.

(56) References Cited

U.S. PATENT DOCUMENTS

| | | |
|---|---|---|
| 2004/0115433 A1 | 6/2004 | Elaissari et al. |
| 2005/0175702 A1 | 8/2005 | Muller-Schulte |
| 2007/0154397 A1 | 7/2007 | Chang et al. |

FOREIGN PATENT DOCUMENTS

DE    19800294    7/1999
(Continued)

OTHER PUBLICATIONS
(http://www.magneticmicrosphere.com/hafeli_lab/other/Bulte_chapter_2001.pdf, accessed Sep. 20, 2013.*
(Continued)

*Primary Examiner* — Paul Dickinson
(74) *Attorney, Agent, or Firm* — Merchant & Gould P.C.

(57) ABSTRACT

The present invention relates to polymer microgel beads having a polymeric matrix with nanomagnetic particles dispersed substantially uniformly therethrough, wherein a steric stabilizer is associated with the particles, the steric stabilizer being a polymeric material that (i) forms at least part of the polymeric matrix of the beads, and (ii) comprises a steric stabilizing polymeric segment and an anchoring polymeric segment, wherein the steric stabilizing polymeric segment is different from the anchoring polymeric segment, and wherein the anchoring polymeric segment has an affinity toward the surface of the nanomagnetic particles and secures the stabilizer to the particles.

23 Claims, 1 Drawing Sheet

(56) References Cited

FOREIGN PATENT DOCUMENTS

| | | |
|---|---|---|
| JP | 2005-537342 | 12/2005 |
| JP | 2006-328309 | 12/2006 |
| JP | 2008-516017 | 5/2008 |
| WO | WO 2004/081072 | 9/2004 |
| WO | WO 2006/037161 | 4/2006 |
| WO | WO 2007/097593 | 8/2007 |
| WO | WO 2007/112503 | 10/2007 |

OTHER PUBLICATIONS

International Search Report of PCT/AU2009/000618, mailed Jul. 13, 2009, 4 pgs.

International Preliminary Report on Patentability of PCT/AU2009/000618, mailed Nov. 17, 2010, 3 pgs.

Arshady, "Microspheres for biomedical applications: preparation of reactive and labelled microspheres", Biomaterials, 1993, vol. 14, No. 1, pp. 5-15.

Cui et al., "Developing a Hybrid Emulsion Polymerization System to Synthesize $Fe_3O_4$/Polystyrene Latexes with Narrow Size Distribution and High Magnetite Content", Journal of Polymer Science: Part A: Polymer Chemistry, Wiley InterScience, 2007, pp. 5285-5295.

Fonnum et al., "Characterisation of Dynabeads® by magnetization measurements and Mössbauer spectroscopy", Journal of Magnetism and Magnetic Materials, 2005, vol. 293, pp. 41-47.

Gu et al., "Preparation and colloidal stability of monodisperse magnetic polymer particles", Journal of Colloid and Interface Science, 2005, vol. 289, pp. 419-426.

Kim et al., "Magnetomicelles: Composite Nanostructures from Magnetic Nanoparticles and Cross-Linked Amphiphilic Block Copolymers", Nanoletters, 2005, vol. 5, No. 10, pp. 1987-1991.

Liu et al., "Preparation of Magnetic Microspheres from Water-in-Oil Emulsion Stabilized by Block Copolymer Dispersant", Biomacromolecules, 2005, vol. 6, pp. 1280-1288.

Mackova et al., "Magnetic Poly(N-isopropylacrylamide) Microspheres by Dispersion and Inverse Emulsion Polymerization", Journal of Polymer Science: Part A: Polymer Chemistry, Wiley InterScience, 2007, vol. 45, pp. 5884-5898.

Pich et al., "Temperature Sensitive Hybrid Microgels with Magnetic Properties", Langmuir, 2004, vol. 20, No. 24, pp. 10706-10711.

Sauzedde et al., "Hydrophilic magnetic polymer latexes. 1. Adsorption of magnetic iron oxide nanoparticles onto various cationic latexes", Colloid Polym Sci, 1999, vol. 277, pp. 846-855.

Sauzedde et al., "Hydrophilic magnetic polymer latexes. 2. Encapsulation of adsorbed iron oxide nanoparticles", Colloid Polym Sci, 1999, vol. 277, pp. 1041-1050.

Shiho et al., "Magnetic compounds as coatings on polymer particles and magnetic properties of the composite particles", Journal of Materials Chemistry, 2000, vol. 10, pp. 333-336.

Wormuth, "Superparamagnetic Latex via Inverse Emulsion Polymerization", Journal of Colloid and Interface Science, 2001, vol. 241, pp. 366-377.

Zhang et al., "Encapsulation of Magnetic Particles Via Miniemulsion Polymerization of Styrene. II. Effect of Some Parameters on the Polymerization of Styrene", Journal of Applied Polymer Science, Wiley InterScience, 2007, vol. 105, pp. 3525-3530.

\* cited by examiner

POLYMER MICROGEL BEADS AND PREPARATIVE METHOD THEREOF

This application is a National Stage Application of PCT/AU2009/000618, filed 15 May 2009, which claims benefit of Serial No. 2008902430, filed 16 May 2008 in Australia and which applications are incorporated herein by reference. To the extent appropriate, a claim of priority is made to each of the above disclosed applications.

FIELD OF THE INVENTION

The present invention relates in general to polymer microgel beads. In particular, the invention relates to polymer microgel beads incorporating nanomagnetic particles, and to a method of preparing the same. The polymer microgel beads in accordance with the invention are particularly suited for use in biomedical applications such as inducing hyperthermia in tissue, and it will therefore be convenient to describe the invention with an emphasis toward these applications. However, it is to be understood that the polymer microgel beads may be used in various other applications.

BACKGROUND OF THE INVENTION

Polymer beads incorporating magnetic particles are known. Such beads have been found to be particularly suitable for use in biomedical applications. In particular, the beads may be used for therapeutic or analytical purposes. For example, magnetic polymer beads may function as a carrier and permit the guiding and release of a drug at a specific site of a subject. The beads may also be used to provide hyperthermic treatment of tissue such as diseased tissue in a subject. Such polymer beads have also found application in immunoassays.

Numerous techniques have been developed over the years to produce polymer beads incorporating magnetic particles. These include layer-by-layer deposition techniques, classical heterogeneous polymerisation processes (e.g. emulsion, suspension, dispersion, microemulsion, and miniemulsion techniques), and the precipitation of magnetic materials within the pores of preformed polymer beads.

For most biomedical applications, it is generally important that the beads be produced with a uniform size and composition and with a relatively high magnetic particle content. Furthermore, it is also generally important that the magnetic particles be substantially uniformly dispersed throughout the polymer bead.

A considerable amount of research has been conducted to date on dispersion techniques for preparing polymer beads incorporating magnetic particles. Such techniques include the aforementioned classical heterogeneous polymerisation processes, which typically involve dispersing magnetic particles in a liquid phase and polymerising monomer to form polymer that encapsulates the particles.

Despite some success, the complexity of polymer particle nucleation in conventional dispersion polymerisation processes and the difficulties associated with controlling the stability of the dispersed magnetic particles have proven to be major obstacles in preparing the polymer beads efficiently and with high magnetic particle content. For example, the principle locus for particle nucleation in conventional emulsion polymerisation processes is generally either in the aqueous phase or in monomer-swollen micelles. However, the presence of magnetic particles dispersed in the aqueous phase can provide for additional nucleation sites at the surface of these particles. Accordingly, competition between these mechanisms can result in the formation of polymer beads with little or no magnetic particle content.

The effectiveness of dispersion techniques can also become problematic as the polymer beads are prepared with progressively small magnetic particles. In particular, as the magnetic particles become smaller (for example ≤100 nm) it becomes increasingly more difficult to maintain the particles in a dispersed state so as to produce beads having the particles substantially uniformly distributed therein (i.e. it becomes difficult to prevent aggregation of the magnetic particles during bead manufacture).

An opportunity therefore remains to address or ameliorate one or more disadvantages or shortcomings associated with existing polymer beads incorporating magnetic particles and/or their methods of manufacture, or to at least provide a useful alternative to conventional polymer beads incorporating magnetic particles and/or their methods of manufacture.

SUMMARY OF THE INVENTION

The present invention therefore provides a method of preparing polymer microgel beads incorporating nanomagnetic particles, the method comprising:
(i) providing a dispersion comprising a continuous organic phase and a dispersed aqueous phase, the dispersed aqueous phase comprising hydrophilic liquid and nanomagnetic particles dispersed throughout the aqueous phase, the nanomagnetic particles being maintained in their dispersed state by a steric stabiliser, wherein the steric stabiliser is a polymeric material comprising:
  (a) a steric stabilising polymeric segment and an anchoring polymeric segment, wherein the steric stabilising polymeric segment is different from the anchoring polymeric segment, and wherein the anchoring polymeric segment has an affinity toward the nanomagnetic particles and secures the steric stabiliser to the particles; and
  (b) one or more reactive functional group;
(ii) removing hydrophilic liquid from the aqueous phase; and
(iii) promoting a reaction between the reactive functional groups of the steric stabilisers to thereby form the polymer microgel beads incorporating the nanomagnetic particles.

It has now been found that the steric stabiliser used in accordance with the invention can function to (i) provide a highly stable dispersion of nanomagnetic particles within the aqueous phase, and (ii) present functional groups that can react with each other so as to tether the stabilisers together and form the polymer matrix of the beads. In particular, upon removing hydrophilic liquid from the aqueous phase, the volume of the dispersed aqueous phase droplets is reduced. This in turn forces nanomagnetic particles in each of the dispersed aqueous phase droplets together so as to place the reactive functional groups of stabilisers anchored to a given particle in proximity for reaction with reactive functional groups of stabilisers anchored to neighbouring particles. Reaction between such functional groups can then afford the polymeric matrix of the microgel beads having the nanomagnetic particles incorporated therein.

The steric stabiliser is particularly effective at stabilising in the aqueous phase nanomagnetic particles of a size of less than about 100 nm for example of less than about 50 nm or less than 20 nm.

The polymer matrix of the microgel beads, which in effect encapsulates the nanomagnetic particles, can advantageously be prepared in a controlled, reproducible and efficient manner. It has therefore been possible to prepare the polymer microgel beads to a desired size with a relatively high (e.g. up to about 80 wt. %, relative to the total mass of the bead) substantially uniformly distributed magnetic particle content.

The present invention therefore also provides polymer microgel beads having a polymeric matrix with nanomagnetic particles dispersed substantially uniformly therethrough, wherein a steric stabiliser is associated with the particles, the steric stabiliser being a polymeric material that (i) forms at least part of the polymeric matrix of the beads, and (ii) comprises a steric stabilising polymeric segment and an anchoring polymeric segment, wherein the steric stabilising polymeric segment is different from the anchoring polymeric segment, and wherein the anchoring polymeric segment has an affinity toward the surface of the nanomagnetic particles and secures the stabiliser to the particles.

The polymer microgel beads in accordance with the invention may be used in a variety of biomedical applications. For example, the beads may be used to treat a disease or condition in a subject.

Accordingly, the present invention also provides a composition suitable for administration to a subject, the composition comprising polymer microgel beads in accordance with the invention and a pharmacologically acceptable carrier.

In one embodiment, the composition in accordance with the invention is for hyperthermia therapy.

In a further embodiment, there is provided use of composition in accordance with the invention for hyperthermia therapy.

In another embodiment, there is provided a method of performing hyperthermia therapy on a target site of interest in a subject, the method comprising administering a composition according to the invention to the subject and exposing at least the target site to a magnetic field of clinically acceptable frequency and strength to promote the hyperthermia therapy.

In a further embodiment, there is provided use of a composition in accordance with the invention in the manufacture of a formulation for performing hyperthermia therapy.

In another embodiment, there is provided a method for heating a target site of interest in a subject, the method comprising:
(i) administering a composition in accordance with the invention to the subject; and
(ii) exposing at least the target site to a magnetic field of a clinically acceptable frequency and strength such that microgel beads from the composition radiate heat at the target site.

In some applications it may be desirable to image the polymer microgel beads once they have been administered to a subject. The beads may therefore comprise a radioactive isotope for imaging purposes.

Further aspects of the invention appear below in the detailed description of the invention.

BRIEF DESCRIPTION OF THE DRAWINGS

The invention will also be described herein with reference to the following non-limiting drawings in which.

DETAILED DESCRIPTION OF THE INVENTION

Figure 1:
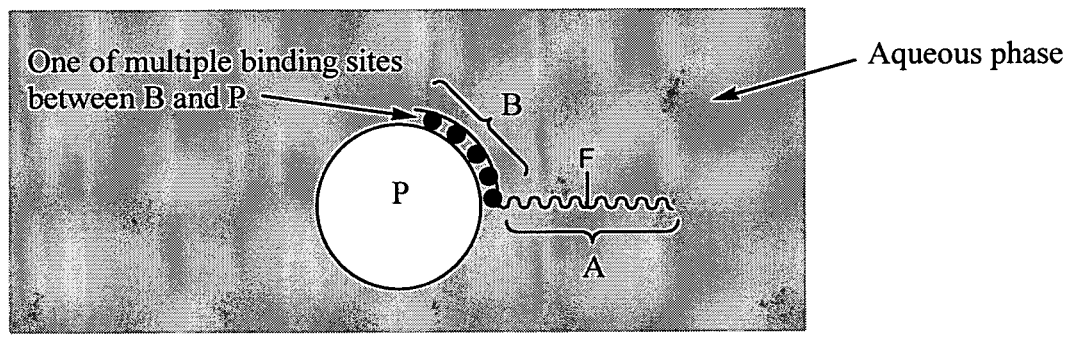
FIG. 1 presents a simplified schematic illustration not to scale showing: the multiple binding interactions between the anchoring polymeric segment (B) and a nanomagnetic particle (P), and the steric stabilising segment (A) solubilised in the aqueous phase and presenting reactive functional group (F)

As used herein, the expression "polymer microgel" is intended to mean a three dimensional network of polymer chains that collectively form a polymer matrix that can absorb and be swollen by an aqueous liquid. The term "beads" used in conjunction with the expression "polymer microgel" is intended to convey that the polymer microgel mass is in the form of a discrete shape. There is no particular limitation regarding the discrete shape the beads may take, but they will generally be spheroidal.

By the beads having a polymer matrix that can absorb and be swollen by an aqueous liquid, it will be appreciated that the polymer chains that form the matrix are in effect tethered together such that they can not be fully solvated (i.e. where the bead structure is destroyed) by the aqueous liquid. The polymer matrix derives such properties at least through the collective composite structure of the beads. In particular, reaction of reactive functional groups of steric stabilisers anchored on a given particle with reactive functional groups of steric stabilisers anchored on neighbouring particles in effect forms a crosslinked composite structure of the stabilisers and particles.

The steric stabilisers may each comprise more than one reactive functional group, the effect of which can in addition promote crosslinking between steric stabilisers per se. The aqueous phase may also comprise polymer chains other than the steric stabilisers which have one or more functional groups that can react with those of the steric stabiliser. Thus, upon removing hydrophilic liquid from the aqueous phase, the functional groups of such polymer chains and the steric stabiliser may react so as to collectively form the polymeric matrix of the beads.

The crosslinked structure of the beads can therefore be seen to be provided by a crosslinked composite structure of the stabilisers and particles and/or a crosslinked structure of the steric stabilisers per se and/or optionally a crosslinked structure of the steric stabilisers and polymer chains other than the steric stabilisers.

As will be discussed in more detail below, the size of the polymer microgel beads may be effectively and efficiently tailored during the method of the invention through control of the size and composition of the aqueous phase droplets dispersed throughout the continuous organic phase.

The size of the beads that are to be produced will generally be dictated by their intended application. Generally, the beads will have a size ranging from about 100 nm to about 200 microns, for example from about 10 to about 100 microns, or from about 10 to about 50 microns. In some applications, it may be desirable that the beads have a size ranging from about 20 to about 50 microns. The beads can advantageously be prepared so as to have a size of less than about 10 microns, for example from about 500 nm to about 10 microns, or from about 1 micron to about 10 microns.

For avoidance of any doubt, reference herein to the "size" of the polymer microgel beads or nanomagnetic particles is intended to denote an average size of the beads or particles based on the largest dimension of a given bead or particle. Polymer microgel beads having a size of about 1 micron or more are to be determined by light microscopy, whereas the nanomagnetic particles and polymer microgel beads having a size of less than about 1 micron are to be determined by Transmission Electron Microscopy (TEM).

The polymer microgel beads in accordance with the invention incorporate nanomagnetic particles. By the beads "incorporating" nanomagnetic particles is meant that the particles are retained within and throughout the polymeric matrix of each polymer microgel bead. The method in accordance with the invention advantageously enables the nanomagnetic particles to be distributed substantially evenly or uniformly throughout the polymeric matrix of the beads. Furthermore, the nanomagnetic particles can be distributed in this manner as individual or primary particles (i.e. in a substantially non-aggregated form throughout each bead).

The polymer microgel beads in accordance with the invention can advantageously have a low through to high nanomagnetic particle content. For example, the beads may contain up to about 10 wt %, or up to about 20 wt %, or up to about 30 wt %, or up to about 40 wt %, or up to about 50 wt %, or up to about 60 wt %, or up to about 70 wt %, or even up to about 80 wt % of nanomagnetic particles, relative to the total mass of the beads. The beads may therefore contain at least 10 wt %, or at least about 20 wt %, or at least about 30 wt %, or at least about 40 wt %, or at least about 50 wt %, or at least about 60 wt %, or even about 70 wt % of nanomagnetic particles, relative to the total mass of the beads.

The nanomagnetic particle content that is to be incorporated in the beads will generally be dictated by the intended application of the beads. For example, where the beads are to be used for providing hyperthermia therapy, or as synonymously used herein hyperthermic treatment, those skilled in the art will appreciate that the volumetric absorption rate (VAR) of the beads should be sufficient under appropriate magnetic field conditions to promote therapeutic heating at a target site. Generally, the VAR of such beads will be at least about 1 Watts/cm$^3$, preferably at least about 10 Watts/cm$^3$, when exposed to a magnetic field of a clinically acceptable frequency and strength.

As used herein, "VAR" is intended to define the heating quality of the polymer microgel beads and is expressed as the amount of heat released by a unit volume of the bead per unit time during exposure to a magnetic field of a defined frequency and field strength.

In terms of the nanomagnetic particle content of the polymer microgel beads, those skilled in the art will appreciate that the ratio of the polymeric matrix of the beads to the nanomagnetic particles can potentially influence the heating efficiency of the beads. For example, as the nanomagnetic particle content of the beads increases there can be a greater potential for the particles to aggregate and thus reduce the effective VAR of the beads. However, the polymer microgel beads in accordance with the invention can advantageously be prepared using a relatively high nanomagnetic particle content with little or no aggregation of the particles. Accordingly, the heating quality of the beads can be maximised for a given nanomagnetic particle content.

The "nanomagnetic particles" used in accordance with the invention are of a size of less than 1 micron. Those skilled in the art will appreciate that the composition and/or size of the particles can influence their magnetic properties. The nanomagnetic particles will generally exhibit ferromagnetic, ferrimagnetic or superparamagnetic properties.

The specific size of the nanomagnetic particles used will generally be dictated by the intended application of the polymer microgel beads. For some applications, it may be desirable for the nanomagnetic particles to be of a size of less than about 500 nm, for example less than about 100 nm, or less than about 50 nm. The method of the present invention has been found to be particularly well suited to producing polymer beads incorporating nanomagnetic particles having a size ranging from about 1 nm to about 40 nm.

Where the polymer microgel beads are to be used for providing hyperthermic treatment, the nanomagnetic particles used will generally have a particle size of less than about 50 nm, for example ranging from about 10 nm to about 40 nm.

There is no particular limitation on the type of nanomagnetic particles that may be used in accordance with the invention. Examples of suitable magnetic materials include, but are not limited to, iron, nickel, chromium, cobalt, oxides thereof or mixtures of any of these. Preferred iron oxide magnetic materials include γ-ion oxide (i.e. $\gamma$-$Fe_2O_3$, also known as maghemite) and magnetite ($Fe_3O_4$).

In some applications, it may be desirable that the polymer microgel beads incorporate nanomagnetic particles that are superparamagnetic (i.e. nano-superparamagnetic particles). As used herein, the term "superparamagnetic" is intended to mean magnetic particles that do not have the following properties; (i) coercivity, (ii) remanence, or (iii) a hysteresis loop when the rate of change of an applied magnetic field is quasi static.

Those skilled in the art will appreciate that the VAR of superparamagnetic particles is proportional to the quadrature component of the complex susceptibility, i.e. $\chi''$. Maximum VAR is obtained when the Néel relaxation time, $\tau_N$, is equal to the inverse of the magnetic field frequency, $\omega$, i.e.

$$\tau_N \omega = 1.$$

In turn, $\tau_N$ is determined by the magnetic anisotropy energy, KV, where K is the magnetic anisotropy and V is the particle volume. The value of K is determined by magnetocrystalline anisotropy or the particle shape if it is not perfectly spherical. This assumes particles are smaller than the critical size for formation of magnetic domains, i.e. they are in the superparamagnetic regime.

The properties of VAR, magnetic susceptibility, magnetic moment and saturation magnetization are measurable by standard methods known to those skilled in the art.

The nanomagnetic particles may be selected from ferrites of general formula $MO.Fe_2O_3$ where M is a bivalent metal such as Fe, Co, Ni, Mn, Be, Mg, Ca, Ba, Sr, Cu, Zn, Pt or mixtures thereof, or magnetoplumbite type oxides of the general formula $MO.6Fe_2O_3$ where M is a large bivalent ion, metallic iron, cobalt or nickel. Additionally, they could be particles of pure Fe, Ni, Cr or Co or oxides of these. Alternatively they could be mixtures of any of these.

In one embodiment, the nanomagnetic particles are particles of iron oxide such as magnetite ($Fe_3O_4$) or maghemite ($\gamma$-$Fe_2O_3$) with a particle size preferably less than 50 nanometers, for example between 1 and 40 nanometers.

In a further embodiment, the nanomagnetic particles are particles of maghemite. Such particles can provide a number of advantages in that maghemite nano particles of optimum size possess a higher VAR than do optimum size magnetite nano particles when subjected to clinically relevant magnetic field conditions, and maghemite is generally a more chemical stable form of iron oxide than magnetite.

Those skilled in the art will appreciate that the higher VAR of maghemite means that a lower nanomagnetic particle content can be used to produce the polymer microgel beads with the required VAR.

Nanomagnetic particles used in accordance with the invention may be conveniently prepared using techniques known in the art.

In accordance with a method of the invention, there is provided a dispersion comprising a continuous organic phase and a dispersed aqueous phase. Those skilled in the art may commonly refer to such a dispersion as an inverse emulsion or a water in oil dispersion. The dispersion used in accordance with the invention may therefore simplistically be described as an organic liquid having droplets of aqueous liquid dispersed therein. The term "phase" is therefore used herein to simply convey that there is an interface between the organic and aqueous liquids formed as a result of the liquids being substantially immiscible.

In isolation, it will be appreciated that organic and aqueous phases will in effect be an organic and aqueous liquid, respectively. In other words, the term phase simply assists with describing these liquids when provided in the form of a dispersion. However, for convenience, the organic and aqueous liquids used to prepare the dispersion may hereinafter simply be referred to as the organic and aqueous phases, respectively. It may also be convenient to refer to the organic and aqueous phases as comprising organic and aqueous solvents, respectively.

The organic phase will generally comprise or be a hydrophobic liquid. Suitable hydrophobic liquids include, but are not limited to, one or more water-immiscible aliphatic or aromatic organic liquids, such as, for example, hydrocarbons having 6 to 20 carbon atoms, kerosene, petrolatums, xylene, toluene, branched-chain isoparaffins and mixtures thereof.

Apart form the dispersed aqueous phase, the continuous organic phase may comprise one or more additives typically employed in the art. For example, it may be necessary to employ a dispersing agent in order to facilitate maintaining the aqueous phase in a dispersed state throughout the continuous organic phase. Those skilled in the art will be able to select a suitable dispersing agent for this purpose.

Suitable dispersing agents will generally be any surfactant that can stabilise the dispersed aqueous phase throughout the continuous organic phase. The dispersing agent is typically added to the organic phase, but can be added to the aqueous phase depending on the solubility of the agent used.

Representatives of such dispersing agents include, but are not limited to, non-ionic surfactants, sorbitan fatty acid esters such as, for example, sorbitan monooleate and sorbitan monolaurate, glycerol esters such as, for example, glycerol monooleate and glycerol monoricinoleate, phthalic esters, partial fatty acid esters of polyglycerol, the reaction product of oleic acid with isopropanolamide, 12-hydroxystearic acid-polyethylene glycol block copolymers (commercially available as Hypermer B246 and Hypermer B261), fatty acid glycerides, glycerin esters, as well as ethoxylated derivatives thereof; cationic surfactants including, but are not limited to, ammonium salts, such as distearyl dimethyl ammonium chloride and dioleyl dimethyl ammonium dichloride; and anionic surfactants such as bis-tri-decyl sulfosuccinic acid salt; or mixtures thereof.

Polymeric dispersing agents are generally preferred, and may be selected from 12-hydroxystearic acid-polyethylene glycol block copolymers, poly(isobutylene) succinic hydride diethylethanol amine (PIBSADEEA), ethylene-co-maleic anhydride, poly(alpha-olefin-co-maleic anhydride), cellulose ethers such as ethyl cellulose, methyl cellulose, hydroxyethyl cellulose, hydroxypropyl cellulose, and carboxyethyl cellulose, poly(lauryl methacrylate-co-acrylic acid), cellulose esters such as acetates, propylonates and butyrates.

The dispersing agents can be used alone or in combination. The dispersing agent is employed in an amount sufficient to maintain the dispersion until the aqueous liquid is removed. The amount and type of dispersing agent(s) employed will vary depending on the composition of the organic and aqueous phases. Those skilled in the art will be able to select a suitable agent(s) and its amount for a given dispersion. Generally, the dispersing agent is employed in an amount not of greater than about 5 wt. % of the total dispersion.

A more detailed discussion concerning the dispersed aqueous phase is provided below, but in general terms it will be appreciated that the aqueous phase will be substantially immiscible in the organic phase. In addition to the nanomagnetic particles, the aqueous phase is also said to comprise hydrophilic liquid. By "hydrophilic liquid" is meant water and liquids miscible with water. By being "aqueous", the aqueous phase will of course comprise water, but it may also comprise one or more other hydrophilic liquids such as methanol, ethanol, dioxane and the like. Reference herein to the aqueous phase comprising "hydrophilic liquid" is therefore intended to be a reference to the liquid composition that forms the aqueous phase droplets.

The aqueous phase will generally not comprise any ethylenically unsaturated monomers.

The dispersion used in accordance with the invention may be prepared using techniques well known in the art. For example, a suitable aqueous liquid may be combined with a suitable organic liquid and subjected to agitation, for example, by some shearing means. As indicated above, a dispersing agent may also be used to facilitate maintaining the resulting aqueous phase in a dispersed state throughout the resulting continuous organic phase. Through the appropriate control of this process, the size of the dispersed aqueous phase droplets can be selected so as to tailor the size of the polymer microgel beads formed in accordance with the method.

The dispersed aqueous phase comprises the nanomagnetic particles dispersed therein. Thus, it will be appreciated that the nanomagnetic particles are in effect dispersed throughout the hydrophilic liquid, which collectively form the aqueous phase dispersed throughout the continuous organic phase. Each dispersed droplet of aqueous phase therefore comprises a substantially uniform distribution of the nanomagnetic particles.

In order to provide the polymer microgel beads with a substantially uniform distribution of the nanomagnetic particles throughout the polymeric matrix of each bead, the nanomagnetic particles are dispersed throughout the aqueous phase. The nanomagnetic particles are maintained in their dispersed state by a steric stabiliser.

The steric stabiliser is a polymeric material in its own right and comprises a steric stabilising polymeric segment and an anchoring polymeric segment. The steric stabilising polymeric segment is different from the anchoring polymeric segment, and the anchoring polymeric segment has an affinity toward the surface of the nanomagnetic particles and secures the stabiliser to the particles. The steric stabiliser also comprises one or more reactive functional groups. The reactive functional groups may reside in the steric stabilising polymeric segment and/or the anchoring polymeric segment. Generally they will reside only in the steric stabilising polymeric segment.

By "reactive functional groups" in the context of the steric stabilisers is meant a functional group presented by one steric stabiliser that can react with a complementary functional group presented by another steric stabiliser so as to form a covalent bond therebetween.

Without wishing to be limited by theory, it is believed that the steric stabiliser used in accordance with the invention forms a strong association with the nanomagnetic particles and provides for a particularly stable dispersion of the particles throughout the aqueous phase. The strong association between the particles and the steric stabiliser is believed to result from the polymeric nature of the anchoring segment of the stabiliser which provides multiple sites for binding interactions between the segment and the particles. The steric stabilising polymeric segment of the stabiliser is believed to promote effective and efficient stabilisation of the particles by providing steric repulsive forces.

The steric stabiliser used in accordance with the invention has been found to be particularly effective at stabilising relatively small nanomagnetic particles (i.e. less than about 100 nm in size) throughout the aqueous phase. In particular, the stabiliser has been found to effectively and efficiently stabilise relatively small nanomagnetic particles in a substantially non-aggregated form throughout the aqueous phase. By virtue of this effective and efficient form of stabilisation, the polymer microgel beads may be prepared in accordance with the invention with a relatively high nanomagnetic particle content (e.g. up to about 80 wt. %) while still maintaining a substantially uniform and non-aggregated distribution of the nanomagnetic particles.

As part of the aqueous phase composition, the nanomagnetic particles are maintained in their dispersed state by a steric stabiliser. By being "maintained" in this context is meant that in the absence of the steric stabiliser the nanomagnetic particles would otherwise flocculate or settle out from the aqueous phase as sediment. In other words, the steric stabiliser functions to retain the nanomagnetic particles in the dispersed state.

The steric stabiliser used in accordance with the invention has a polymeric composition. There is no particular limitation on the molecular weight of the steric stabiliser, and this feature of the stabiliser may be dictated in part by the nature of the nanomagnetic particles that it is destined to stabilise. Generally, the steric stabiliser will have a number average molecular weight of less than about 50,000.

In some embodiments of the invention, it may be preferable that the number average molecular weight of the steric stabiliser is less than about 30,000, or less than about 20,000, or less than about 10,000 or even less than about 5,000. The number average molecular weight of the steric stabiliser may also range from about 2,000 to about 3,000.

Steric stabilisers used in accordance with the invention having a relatively low number average molecular weight (e.g. less than about 5,000, preferably in the range of from about 2,000 to about 3,000) have been found to be particularly effective at stabilising relatively small nanomagnetic particles (i.e. particles of less than about 100 nm in size).

Molecular weight values defined herein are those determined using gel permeation chromatography (GPC).

The amount of steric stabiliser used relative to the nanomagnetic particles will vary depending on the nature of the particles, particularly their size. For example, 1 g of 5 nm nanomagnetic particles will require more stabiliser than 1 g of 1 micron nanomagnetic particles due to their increased surface area. Those skilled in the art will be able to determine the required amount of stabiliser for the selected nanomagnetic particles.

The steric stabiliser used in accordance with the invention is a polymeric material that may be prepared by any suitable polymerisation technique.

In one embodiment at least one of the steric stabilising and anchoring polymeric segments that make up the steric stabiliser are derived from one or more ethylenically unsaturated monomers that have been polymerised by a living polymerisation technique. Employing at least one such segment is believed to enhance the stabilising properties of the steric stabiliser. Further detail regarding suitable living polymerisation techniques is discussed below. Where only one of the segments is derived in this manner, the other segment may be derived by any other conventional polymerisation technique known by those skilled in the art.

By "steric stabilising polymeric segment" is meant a segment or region of the steric stabiliser that is polymeric (i.e. formed by the polymerisation of at least one type of monomer) and that provides for the steric stabilising function of the steric stabiliser. For convenience, the steric stabilising polymeric segment may herein after be referred to polymeric segment "A".

As alluded to above, the steric stabilising polymeric segment functions to stabilise the particular material throughout the aqueous phase by providing steric repulsion forces.

By being polymeric, it will be appreciated that the steric stabilising segment comprises polymerised monomer residues. Thus, the segment will comprise polymerised monomer residues that give rise to the required steric stabilising properties. The polymerised monomer residues that make up the steric stabilising polymeric segment may be the same or different.

The steric stabilising polymeric segment may be substituted with a moiety (e.g. an optional substituent as herein defined), or contain a polymerised monomer residue, that gives rise to electrostatic stabilising properties.

Where the steric stabilising segment comprises the one or more reactive functional groups, the segment may comprise one or more polymerised monomer residues that present the reactive functional group. Alternatively, the segment may be substituted with the reactive functional group after it has been prepared. In that case, the segment will of course be prepared such that it can be readily substituted.

In order to provide the desired steric stabilising effect, the steric stabilising polymeric segment will of course be soluble in the aqueous phase. Determining the solubility of a given steric stabilising polymeric segment in a given aqueous phase can readily be determined by simply preparing the polymeric segment in isolation and conducting a suitable solubility test in the chosen aqueous solvent.

The steric stabiliser as a whole, may or may not be soluble in the chosen aqueous solvent, but will none the less present a steric stabilising polymeric segment that is.

Those skilled in the art will have an understanding of polymeric materials that may be employed as the steric stabilising polymeric segment, as to the monomers that may be polymerised to form such polymers. For example, suitable polymeric materials include, but are not limited to, polyacrylamide, polyethylene oxide, polyhydroxyethylacrylate, poly N-isopropylacrylamide, polydimethylaminoethylmethacrylate, polyvinyl pyrrolidone and copolymers thereof. Thus, suitable monomers that may be used to form the stabilising polymeric segment include, but are not limited to, acrylamide, ethylene oxide, hydroxyethylacrylate, N-isopropylacrylamide, dimethylaminoethylmethacrylate, vinyl pyrrolidone and combinations thereof.

Where the steric stabilising segment is to comprise the one or more reactive functional groups, it is preferable that the segment be prepared such that it comprises one or more polymerised monomer residues that present the reactive functional group. In that case, suitable monomers that will present a suitable reactive functional group include, but are not limited to, acetoacetoxyethyl methacrylate, glycidyl methacrylate, N-methylolacrylamide, (isobutoxymethyl)acrylamide, hydroxyethyl acrylate, t-butyl-carbodiimidoethyl methacrylate, acrylic acid, γ-methacryloxypropyltriisopropoxysilane, 2-isocyanoethyl methacrylate and diacetone acrylamide, and combinations thereof.

Examples of pairs of monomers mentioned directly above that can be used to present the required complementary reactive functional groups of the steric stabilisers include N-methylolacrylamide and itself, (isobutoxymethyl)acrylamide and itself, γ-methacryloxypropyltriisopropoxysilane and itself, 2-isocyanoethyl methacrylate and hydroxyethyl acrylate, and t-butyl-carbodiimidoethyl methacrylate and acrylic acid.

By being able to select a specific steric stabilising polymeric segment independent of the anchoring polymeric segment, the steric stabilisers used in accordance with the invention can advantageously be tailor designed to suit a particular aqueous phase and thereby maximise the steric stabilising properties of the steric stabiliser.

Although there is no particular limitation on the polymerisation technique that may be used to prepare the steric stabilising segment, a living polymerisation technique can afford a number of advantages. Those skilled in the art will appreciate that "living polymerisation" is a form of addition polymerisation whereby chain growth propagates with essentially no chain transfer and essentially no termination that give rise to dead polymer chains. By a "dead polymer chain" is meant one that can not undergo further addition of monomers.

In a living polymerization, typically all polymer chains are initiated at the start of the polymerization with minimal new chains being initiated in latter stages of the polymerization. After this initiation process, all the polymer chains in effect grow at the same rate. Characteristics and properties of a living polymerization generally include (i) the molecular weight of the polymer increases with conversion, (ii) there is a narrow distribution of polymer chain lengths (i.e. they are of similar molecular weight), and (iii) additional monomers can be added to the polymer chain to create block co-polymer structures. Thus living polymerisation enables excellent control over molecular weight, polymer chain architecture and polydispersity of the resulting polymer that can not be achieved with non-living polymerization methods.

Suitable living polymerisation techniques may be selected from ionic polymerisation and controlled radical polymerisation (CRP). Examples of CRP include, but are not limited to, iniferter polymerisation, stable free radical mediated polymerisation (SFRP), atom transfer radical polymerisation (ATRP), and reversible addition fragmentation chain transfer (RAFT) polymerisation.

Living ionic polymerisation is a form of addition polymerisation whereby the kinetic-chain carriers are ions or ion pairs. The polymerisation proceeds via anionic or cationic kinetic-chain carriers. In other words, the propagating species will either carry a negative or positive charge, and as such there will also be an associated counter cation or counter anion, respectively. For example, in the case of anionic polymerisation, the polymerisation may be conducted using a moiety represented as I$^-$M$^+$, where I represents an organo-anion (e.g. an optionally substituted alkyl anion) and M represents an associated countercation, or in the case of living cationic polymerisation, the moiety might be represented as I$^+$M$^-$, where I represents an organo-cation (e.g. an optionally substituted alkyl cation) and M represents an associated counteranion. Suitable moieties for conducting anionic and cationic living polymerisation are well known to those skilled in the art.

The living polymerisation technique may be a CRP technique.

Iniferter polymerisation is a well known form of CRP, and is generally understood to proceed by a mechanism illustrated below in Scheme 1.

Scheme 1: General mechanism of controlled radical polymerisation with iniferters.

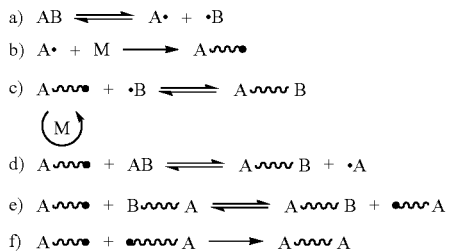

With reference to Scheme 1, the iniferter AB dissociates chemically, thermally or photochemically to produce a reactive radical species A and generally a relatively stable radical species B (for symmetrical iniferters the radical species B will be the same as the radical species A) (step a). The radical species A can initiate polymerisation of monomer M (in step b) and may be deactivated by coupling with radical species B (in step c). Transfer to the iniferter (in step d) and/or transfer to dormant polymer (in step e) followed by termination (in step f) characterise iniferter chemistry.

Suitable moieties for conducting iniferter polymerisation are well known to those skilled in the art, and include, but are not limited to, dithiocarbonate, disulphide, and thiuram disulphide moieties.

SFRP is a well known form of CRP, and is generally understood to proceed by a mechanism illustrated below in Scheme 2.

Scheme 2: General mechanism of controlled radical polymerisation with stable free radical mediated polymerisation.

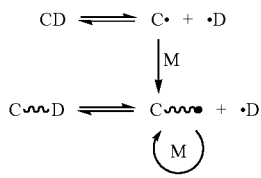

With reference to Scheme 2, SFRP moiety CD dissociates to produce an active radical species C and a stable radical species D. The active radical species C reacts with monomer M, which resulting propagating chain may recombine with the stable radical species D. Unlike iniferter moieties, SFRP moieties do not provide for a transfer step.

Suitable moieties for conducting SFRP are well known to those skilled in the art, and include, but are not limited to, moieties capable of generating phenoxy and nitroxy radicals. Where the moiety generates a nitroxy radical, the polymerisation technique is more commonly known as nitroxide mediated polymerisation (NMP).

Examples of SFRP moieties capable of generating phenoxy radicals include those comprising a phenoxy group substituted in the 2 and 6 positions by bulky groups such as tert-alkyl (e.g. t-butyl), phenyl or dimethylbenzyl, and optionally substituted at the 4 position by an alkyl, alkyloxy, aryl, or aryloxy group or by a heteroatom containing group (e.g. S, N or O) such dimethylamino or diphenylamino group. Thiophenoxy analogues of such phenoxy containing moieties are also contemplated.

SFRP moieties capable of generating nitroxy radicals include those comprising the substituent $R^1R^2N$—O—, where $R^1$ and $R^2$ are tertiary alkyl groups, or where $R^1$ and $R^2$ together with the N atom form a cyclic structure, preferably having tertiary branching at the positions α to the N atom. Examples of such nitroxy substituents include 2,2,5,5-tetraalkylpyrrolidinoxyl, as well as those in which the 5-membered heterocycle ring is fused to an alicyclic or aromatic ring, hindered aliphatic dialkylaminoxyl and iminoxyl substituents. A common nitroxy substituent employed in SFRP is 2,2,6,6-tetramethyl-1-piperidinyloxy.

ATRP is a well known form of CRP, and generally employs a transition metal catalyst to reversibly deactivate a propagating radical by transfer of a transferable atom or group such as a halogen atom to the propagating polymer chain, thereby reducing the oxidation state of the metal catalyst as illustrated below in Scheme 3.

Scheme 3: General mechanism of controlled radical polymerisation with atom transfer radical polymerisation.

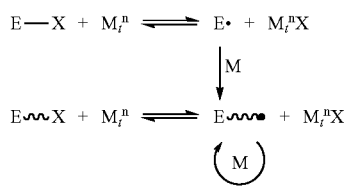

With reference to Scheme 3, a transferable group or atom (X, e.g. halide, hydroxyl, $C_1$-$C_6$-alkoxy, cyano, cyanato, thiocyanato or azido) is transferred from the organic compound (E) (e.g. optionally substituted alkyl, optionally substituted aryl, optionally substituted alkylaryl, or the polymer chain) to a transition metal catalyst ($M_t$, e.g. copper, iron, gold, silver, mercury, palladium, platinum, cobalt, manganese, ruthenium, molybdenum, niobium, or zinc) having oxidation number (n), upon which a radical species is formed that initiates polymerisation with monomer (M). As part of this process, the metal complex is oxidised ($M_t^{n+1}X$). A similar reaction sequence is then established between the propagating polymer chain and the dormant X end-capped polymer chains.

RAFT polymerisation is well known in the art and is believed to operate through the mechanism outlined below in Scheme 4.

Scheme 4: General mechainism of controlled radical polymerisation with reversible addition fragmentation chain transfer polymerisation.

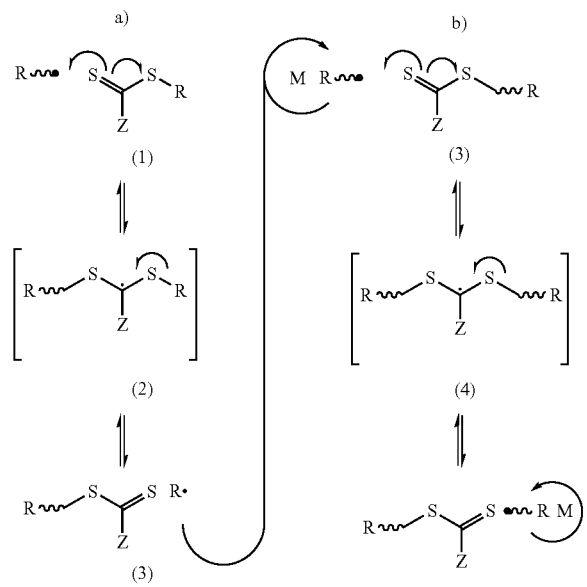

With reference to Scheme 4, RAFT polymerisation is believed to proceed through initial reaction sequence (a) that involves reaction of a RAFT moiety (1) with a propagating radical. The labile intermediate radical species (2) that is formed fragments to form a temporarily deactivated dormant polymer species (3) together a radical (R) derived from the RAFT moiety. This radical can then promote polymerisation of monomer (M), thereby reinitiating polymerisation. The propagating polymer chain can then react with the dormant polymer species (3) to promote the reaction sequence (b) that is similar to reaction sequence (a). Thus, a labile intermediate radical (4) is formed and subsequently fragments to form again a dormant polymer species together with a radical which is capable of further chain growth.

RAFT moieties generally comprise a thiocarbonylthio group (which is a divalent moiety represented by: —C(S)S—) and include xanthates, dithioesters, dithiocarbonates, dithiocarbanates and trithiocarbonates.

The steric stabilising polymeric segment may be formed by the polymerisation of one type of monomer or a combination of two or more different monomers. Accordingly, the steric stabilising polymeric segment may be a homopolymeric segment or a copolymeric segment.

Given that the stabilising polymeric segment forms only part of the steric stabiliser, rather than defining the steric stabilising polymeric segment in terms of its number average molecular weight, it can instead be useful to make reference to the number of polymerised monomeric units that collectively form the segment. Thus, although there is no particular limitation on the number of such units that collectively form the steric stabilising polymeric segment, in some embodiments of the invention it may be desirable that the steric stabiliser has a relatively low number average molecular weight. In that case, it is preferable that the steric stabilising polymeric segment has less than about 50, more preferably less than about 40, most preferably from about 15 to about 30 polymerised monomer residue repeat units that make up the overall segment.

In one embodiment, at least one, preferably at least two, more preferably at least 3 of the polymerised monomer residue repeat units that make up the steric stabilising polymeric segment is a polymerised residue of a monomer that presents a reactive functional group as hereinbefore described.

By an "anchoring polymeric segment" is meant a segment or region of the steric stabiliser that is polymeric and that has an affinity toward the surface of the nanomagnetic particles and functions to secure the steric stabiliser to the particles. For convenience, the anchoring polymeric segment may hereinafter be referred to as polymeric segment "B".

By being polymeric, it will be appreciated that the anchoring segment comprises polymerised monomer residues. In particular, the segment will comprise polymerised monomer residues that give rise to the required binding affinity toward the nanomagnetic particles. The polymerised monomer residues that make up the anchoring polymeric segment may be the same or different.

It is believed that the ability of the anchoring segment to present multiple sites for binding interactions with the nanomagnetic particles at least in part gives rise to the excellent stabilising properties provided by the steric stabiliser.

Generally, the anchoring segment will have at least two polymerised monomer residues that each provides a site for binding with the nanomagnetic particles, preferably at least three, more preferably at least five, still more preferably at least seven, most preferably at least ten of such polymerised monomer residues. Not all of the polymerised monomer residues that make up the anchoring segment are necessarily required to give rise to a binding interaction with the particles, but it is generally preferred that the majority if not all of the polymerised monomer residues that make up the anchoring segment do give rise to a binding interaction with the particles.

The anchoring segment may therefore be described as having multiple sites that collectively secure the stabiliser to the particulate material.

The anchoring polymeric segment can also be substituted with a moiety (e.g. an optional substituent as herein defined) that may or may not give rise to a binding interaction with the nanomagnetic particles.

Where the anchoring polymeric segment comprises the one or more reactive functional groups, the segment may comprise one or more polymerised monomer residues that present a reactive functional group as hereinbefore described in respect of the steric stabilising polymeric segment. Alternatively, the anchoring polymeric segment may be substituted with a reactive functional group after it has been prepared. In that case, the segment will of course be prepared such that it can be readily substituted.

In order to provide the desired anchoring effect, the anchoring polymeric segment will have a binding affinity toward the nanomagnetic particles. The specific mode by which the anchoring segments bind to the particles is not particularly important, for example it might be by way of electrostatic forces, hydrogen bonding, ionic charge, Van der Waals forces, or any combination thereof. A particular advantage provided by the anchoring polymeric segment is that it can provide multiple sites for binding interactions with the particles. Thus, even where a given binding site only provides a relatively weak interaction with the particles, the presence of multiples of such sites within the segment enables it as a whole to bind securely with the particles.

The specific anchoring polymeric segment required will generally be dictated to the nature of the nanomagnetic particles to which it is to bind. When describing the interaction of the anchoring polymeric segment with the particles, it can be convenient to refer to the hydrophilic and hydrophobic character of the segment and the particles. Thus, in general, suitable binding interactions will occur when the segment and the particles have similar hydrophilic or hydrophobic character. For example, where the particles have a relatively hydrophilic surface (e.g. its surface can be wetted with an aqueous solution), then good binding should be attained using an anchoring polymeric segment that has hydrophilic character (e.g. in its isolated form the segment would be soluble in an aqueous medium). Such an example might be realised where the particles are of a type that can form a charge on their surface. In that case, it may be desirable for the segment to comprise polymerised residues of monomers that can also form a charge (e.g. residues of an ionisable monomer) so as to promote ionic binding between the segment and the particles. Promoting the formation of such charged species might be facilitated by adjusting the pH of the aqueous phase in which the stabiliser and particles reside.

Nanomagnetic particles used in accordance with the invention will generally have a relatively hydrophilic surface, and may be capable of forming a charge on their surface. In that case, the anchoring polymeric segment will preferably comprise polymerised residues of an ionisable monomer.

By the term "ionisable monomer" is meant that the monomer comprises a functional group which can be ionised in solution to form a cationic or anionic group. Such functional groups will generally be capable of being ionised under acidic or basic conditions through loss or acceptance of a proton. Generally, the functional groups are acid groups or basic groups. For example, a carboxylic acid functional group may form a carboxylate anion under basic conditions, and an amine functional group may form a quaternary ammonium cation under acidic conditions. The functional groups may also be capable of being ionised through an ion exchange process.

Examples of suitable ionisable monomers having acid groups include, but are not limited to, methacrylic acid, acrylic acid, itaconic acid, p-styrene carboxylic acids, p-styrene sulfonic acids, vinyl sulfonic acid, vinyl phosphonic acid, monoacryloxyethyl phosphate, 2-(methacryloyloxy) ethyl phosphate, ethacrylic acid, alpha-chloroacrylic acid, crotonic acid, fumaric acid, citraconic acid, mesaconic acid, and maleic acid. Examples of suitable ionisable monomers which have basic groups include, but are not limited to, 2-(dimethyl amino)ethyl and propyl acrylates and methacrylates, and the corresponding 3-(diethylamino)ethyl and propyl acrylates and methacrylates.

Those skilled in the art will be able to select an appropriate anchoring polymeric segment to bind with the surface of the selected nanomagnetic particles.

By being able to select a specific anchoring polymeric segment independent of the steric stabilising polymeric segment, the steric stabilisers used in accordance with the invention can advantageously be tailor designed to suit particular nanomagnetic particles and thereby maximise the anchoring properties of the steric stabiliser.

Those skilled in the art will appreciate the variety of polymeric materials that may be employed as the anchoring polymeric segment, as to the monomers that may be polymerised to form such polymers. For example, suitable polymeric materials include, but are not limited to, polyacrylic acid, polymethacrylic acid, polystyrene, polyitaconic acid, poly-p-styrene carboxylic acids, poly-p-styrene sulfonic acids, polyvinyl sulfonic acid, polyvinyl phosphonic acid, poly monoacryloxyethyl phosphate, poly-2-(methylacryloyloxy) ethyl phosphate, polyethacrylic acid, poly-alpha-chloroacrylic acid, polycrotonic acid, polyfumaric acid, polycitraconic acid, polymesaconic acid, polymaleic acid, poly-2-(dimethyl amino)ethyl and propyl acrylates and methacrylates, the corresponding poly-3-(diethylamino) ethyl and propyl acrylates and methacrylates, hydrophobic acrylate and methacrylate polymers, polydimethylaminoethylmethacrylate, and copolymers thereof. Thus, suitable monomers that may be used to form the anchoring polymeric segment include, but are not limited to, acrylic acid, methacrylic acid, itaconic acid, p-styrene carboxylic acids, p-styrene sulfonic acids, vinyl sulfonic acid, vinyl phosphonic acid, monoacryloxyethyl phosphate, 2-(methylacryloyloxy) ethyl phosphate, ethacrylic acid, alpha-chloroacrylic acid, crotonic acid, fumaric acid, citraconic acid, mesaconic acid, maleic acid, 2-(dimethyl amino)ethyl and propyl acrylates and methacrylates, the corresponding 3-(diethylamino)ethyl and propyl acrylates and methacrylates, styrene, hydrophobic acrylate and methacrylate monomers, dimethylaminoethylmethacrylate, and combinations thereof.

Where the anchoring polymeric segment is to comprise the one or more reactive functional groups, the segment may be prepared such that it comprises one or more polymerised monomer residues that present a reactive functional group as hereinbefore described in respect of the steric stabilising polymeric segment. However, it is preferable that the one or more reactive functional groups reside in the steric stabilising segment.

There is no particular limitation on the polymerisation technique that may be used to prepare the anchoring polymeric segment. Living polymerisation techniques such as those herein described have been found particularly useful in preparing the anchoring polymeric segment. Where at least one of the steric stabilising and anchoring polymeric segments are derived from one or more ethylenically unsaturated monomers that have been polymerised by a living polymerisation technique, it will preferably be the anchoring segment.

In one embodiment, both the steric stabilising and anchoring polymeric segments are derived from one or more ethylenically unsaturated monomers that have been polymerised by a living polymerisation technique.

The anchoring polymeric segment may be formed by the polymerisation of one type of monomer or a combination of two or more different monomers. Accordingly, the anchoring polymeric segment may be a homopolymeric segment or a copolymeric segment.

Given that the anchoring polymeric segment forms only part of the steric stabiliser, rather than defining the anchoring polymeric segment in terms of its number average molecular weight, it can instead be useful to make reference to the number of polymerised monomeric units that collectively form the segment. Thus, although there is no particular limitation on the number of such units that collectively form the anchoring polymeric segment, in some embodiments of the invention it may be desirable that the steric stabiliser has a relatively low number average molecular weight. In that case, it is preferable that the anchoring polymeric segment has less than about 50, more preferably less than about 40, still more preferably less than about 30, even more preferably from about 5 to about 25, most preferably from about 5 to about 15 polymerised monomer residue repeat units that make up the overall segment.

In one embodiment, at least one, preferably at least two, more preferably at least 3 of the polymerised monomer residue repeat units that make up the anchoring polymeric segment is a polymerised residue of a monomer that presents a reactive functional group as hereinbefore described in respect of the steric stabilising polymeric segment.

Provided that the stabiliser functions as herein described, there is no particular limitation on how the stabilising polymeric segment and the anchoring polymeric segment are to be spatially arranged.

While the steric stabilising polymeric segment and the anchoring polymeric segment may be coupled to each other by any suitable means to form the steric stabiliser, generally they will be directly coupled to each other via a covalent bond and therefore the stabiliser can be simplistically described as or comprising an A-B block copolymer. In that case, A represents the steric stabilising polymeric segment and B represents the anchoring polymeric segment. It will be appreciated from the description above that each of A and B can independently be a homopolymer or a copolymer (e.g. random, block, tapered, etc.).

The stabiliser may comprise more than one steric stabilising polymeric segment (A) and more than one anchoring polymeric segment (B). For example, the stabiliser may be described as or comprising an A-B-A block copolymer. In that case, each A represents the steric stabilising polymeric segment, which may be the same or different, and B represents the anchoring polymeric segment. The stabiliser might also be described as or comprising a B-A-B block copolymer, where each B represents the anchoring polymeric segment, which may be the same or different, and A represents the steric stabilising polymeric segment that is of sufficient chain length such that it forms a "loop" that extends into the aqueous phase and performs its stabilising role.

The stabiliser may also have more complex structures such as star and comb polymer structures. In that case, the anchoring polymeric segment B might represent the main polymer backbone of such structures, with multiple steric stabilising polymeric segments A being attached thereto.

The interaction of a steric stabiliser used in accordance with the invention (in the form of an A-B block copolymer structure) with a nanomagnetic particle in the aqueous phase might be illustrated in the not to scale simplified schematic shown in FIG. 1.

With reference to FIG. 1, the steric stabiliser represented by an A-B block copolymer exhibits an affinity toward the surface of the nanomagnetic particle (P) through the anchoring polymeric segment (B). The anchoring polymeric segment (B) therefore secures the steric stabiliser to the particle. The anchoring polymeric segment (B) provides multiple sites for binding interactions between the segment and the particle. The steric stabilising polymeric segment (A), which is different to segment (B), is soluble in the aqueous phase and (i) functions to maintain the particle dispersed throughout the aqueous phase, and (ii) presents a reactive functional group (F). It will be appreciated that in practice the surface of the particle will have many steric stabilisers secured thereto, and that these have been omitted from the illustration in FIG. 1 for clarity.

Figure 2:
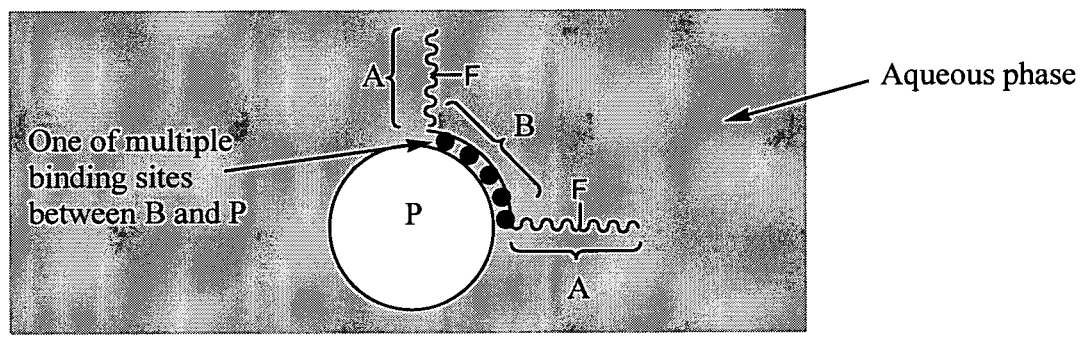
FIG. 2 presents a simplified schematic illustration not to scale showing: the multiple binding interactions between the anchoring polymeric segment (B) and the nanomagnetic particle (P), and the steric stabilising segments (A) solubilised in the aqueous phase, each segment (A) presenting a reactive functional group (F).

A similar illustration to that in FIG. 1 is shown in FIG. 2 where the steric stabiliser used in accordance with the invention is in the form of an A-B-A block copolymer.

As a block copolymer, the steric stabiliser used in accordance with the invention may be prepared by any suitable polymerisation technique. Having regard to the requirements of the polymeric segments A and B, those skilled in the art will be able to prepare suitable block copolymers using techniques well known in the art.

In one embodiment, the steric stabilising polymeric segment and/or the anchoring polymeric segment of the steric stabiliser used in accordance with the invention is prepared using a living polymerisation technique as herein described. In a further embodiment, at least the anchoring polymeric segment of the steric stabiliser used in accordance with the invention is prepared using a living polymerisation technique as herein described. Of the living polymerisation techniques described herein, RAFT polymerisation is preferred.

RAFT polymerisation is a well described radical polymerisation technique that enables polymers to be prepared having a well defined molecular architecture and a low poly dispersity. RAFT polymerisation is conducted using a RAFT agent, and polymers formed under the control of the RAFT agent (i.e. polymerised via a RAFT mechanism to form polymer) may be conveniently referred to as a "RAFT polymer" or a "RAFT derived polymer".

In one embodiment of the invention, the steric stabiliser is a RAFT derived polymer.

Those skilled in the art will appreciate that RAFT agents are commonly depicted as having the general structure Z—C(S)—S—R, and that on formation a RAFT derived polymer will comprise the reaction residue of the RAFT agent. A steric stabiliser used in accordance with the invention might therefore have a structure depicted by general formula (I):

where X represents the polymeric structure of the steric stabiliser (e.g. having a A-B or B-A block copolymer structure as hereinbefore described), $R^1$ and Z are groups derived from the RAFT agent used in preparing the steric stabiliser and are independently selected such that it can function as a RAFT agent in the polymerisation of the monomers that give rise to X.

In order to function as a RAFT agent in the polymerisation of the one or more ethylenically unsaturated monomers, those skilled in the art will appreciate that $R^1$ will typically be an organic group that functional as a free radical leaving group under the polymerisation conditions employed and yet, as a free radical leaving group, retains the ability to reinitiate polymerisation. Similarly, those skilled in the art will appreciate that Z will typically be an organic group that functions to give a suitably high reactivity of the C=S moiety in the RAFT agent towards free radical addition without slowing the rate of fragmentation of the RAFT-adduct radical to the extent that polymerisation is unduly retarded.

Examples of suitable $R^1$ groups include alkyl, alkylaryl, alkoxyaryl, and alkoxyheteroaryl, each of which is optionally substituted with one or more hydrophilic groups.

More specific examples of suitable $R^1$ groups can include $C_1$-$C_6$ alkyl, $C_1$-$C_6$ alkyl aryl, and $C_1$-$C_6$ alkoxy aryl or heteroaryl, each of which is optionally substituted with one or more hydrophilic groups selected from —$CO_2H$, —$CO_2RN$, —$SO_3H$, —$OSO_3H$, —SORN, —$SO_2RN$, —OP(OH)$_2$, —P(OH)$_2$, —PO(OH)$_2$, —OH, —ORN, —(OCH$_2$—CHR)$_w$—OH, —CONH$_2$, CONHR', CONR'R", —NR'R", —N$^+$R'R"R''', where R is selected from $C_1$-$C_6$ alkyl, w is 1 to 10, R', R" and R''' are independently selected from alkyl and aryl which are optionally substituted with one or more hydrophilic substituents selected from —$CO_2H$, —$SO_3H$, —$OSO_3H$, —OH, —(COCH$_2$CHR), —OH, —CONH$_2$, —SOR and SO$_2$R, and salts thereof, R and w are as defined above. Preferred $R^1$ groups include, but are not limited to, —CH(CH$_3$)CO$_2$H, —CH(CO$_2$H)CH$_2$CO$_2$H, —C(CH$_3$)$_2$CO$_2$H.

Suitable Z groups may be selected from optionally substituted alkoxy, optionally substituted aryloxy, optionally substituted alkyl, optionally substituted aryl, optionally substituted heterocyclyl, optionally substituted arylalkyl, optionally substituted alkylthio, optionally substituted arylalkylthio, dialkoxy- or diaryloxy-phosphinyl [—P(=O)OR$^2$$_2$], dialkyl- or diaryl-phosphinyl [—P(=O)R$^2$$_2$], optionally substituted acylamino, optionally substituted acylimino, optionally substituted amino, $R^1$—(X)—S— and a polymer chain formed by any mechanism, for example polyalkylene oxide polymers such as water soluble polyethylene glycol or polypropylene glycol, and alkyl end capped derivatives thereof, where $R^1$ and X are as defined above and $R^2$ is selected from optionally substituted $C_1$-$C_{18}$ alkyl, optionally substituted $C_2$-$C_{18}$ alkenyl, optionally substituted aryl, optionally substituted heterocyclyl, optionally substituted aralkyl, and optionally substituted alkaryl. Preferred Z groups include, but are not limited to, —CH$_2$(C$_6$H$_5$), $C_1$-$C_{20}$ alkyl,

where e is 2 to 4, and —SR$^3$, where R$^3$ is selected from $C_1$ to $C_{20}$ alkyl.

Preferred optional substituents for $R^2$ and Z groups include epoxy, hydroxy, alkoxy, acyl, acyloxy, carboxy (and salts), sulfonic acid (and salts), alkoxy- or aryloxy-carbonyl, isocyanato, cyano, silyl, halo, and dialkylamino.

In selecting both $R^1$ and Z groups of formula (I), all combinations of preferred $R^1$ and Z groups are also preferred.

Where the hydrophilic group is —N$^+$R'R"R''' there will be an associated counter anion.

$R^1$ may also be an organic group optionally substituted with one or more hydrophobic groups. In that case, Z is preferably an organic group optionally substituted with one or more hydrophilic groups.

As used herein, the terms "aryl" and "heteroaryl" refer to any substituent which includes or consists of one or more aromatic or heteroaromatic ring respectively, and which is attached via a ring atom. The rings may be mono or polycyclic ring systems, although mono or bicyclic 5 or 6 membered rings are preferred. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, benzofuran, pyrene, isobenzofuran, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted.

In this specification "optionally substituted" means that a group may or may not be further substituted with one or more groups selected from, but not limited to, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, acetyleno, carboximidyl, haloaryloxy, isocyano, cyano, formyl, carboxyl, nitro, nitroalkyl, nitroalkenyl, nitroalkynyl, nitroaryl, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphonyl, arylsulphonyl, alkylsolphinyl, arylsulphinyl, carboalkoxy, alkylthio, benzylthio, acylthio, sulphonamido, sulfanyl, sulfo and phosphorus-containing groups, alkoxysilyl, silyl, alkylsilyl, alkylalkoxysilyl, phenoxysilyl, alkylphenoxysilyl, alkoxyphenoxysilyl, arylphenoxysilyl, allophanyl, guanidino, hydantoyl, ureido, and ureylene.

Unless stated otherwise, the terms "halogen" and "halo" used herein refer to I, Br, Cl and F.

In this specification the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

As used herein, the term "salt" denotes a species in ionised form, and includes both acid addition and base addition salts. In the context of forming a RAFT polymer, suitable salts are those that do not interfere with the RAFT chemistry.

As used herein, the term "counter anion" denotes a species capable of providing a negative charge to balance the charge of the corresponding cation. Examples of counter anions include, $Cl^-$, $I^-$, $Br^-$, $F^-$, $NO_3^-$, $CN^-$ and $PO_3^-$.

As used herein, the term "alkoxy" denotes straight chain or branched alkoxy, preferably $C_{1-20}$ alkoxy. Examples of alkoxy include methoxy, ethoxy, n-propoxy, isopropoxy and the different butoxy isomers.

As used herein, the term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

As used herein, the term "alkynyl" denotes groups formed from straight chain, branched or cyclic alkyne including those structurally similar to the alkyl and cycloalkyl groups as previously defined, preferably $C_{2-20}$ alkynyl. Examples of alkynyl include ethynyl, 2-propynyl and 2- or 3-butynyl.

As used herein, the term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

As used herein, the terms "heterocyclic", "heterocyclyl" and "heterocycle" used on their own or as part of a term such as "heterocyclicalkenoyl", "heterocycloxy" or "haloheterocyclyl" refer to aromatic, pseudo-aromatic and non-aromatic rings or ring systems which contain one or more heteroatoms selected from N, S, and O and which may be optionally substituted. Preferably the rings or ring systems have 3 to 20 carbon atoms. The rings or ring systems may be selected from those described above in relation to the definition of "heteroaryl".

Preferred steric stabilisers of formula (I) include, but are not limited to, the following general formulas (II) to (X):

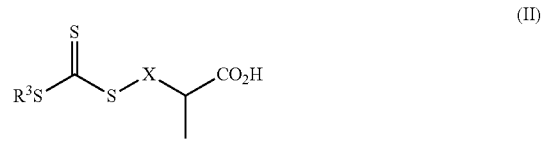

(II)

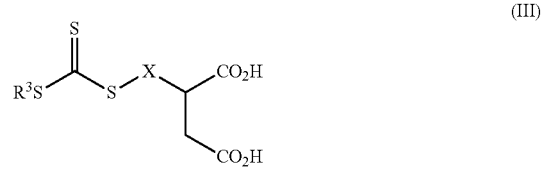

(III)

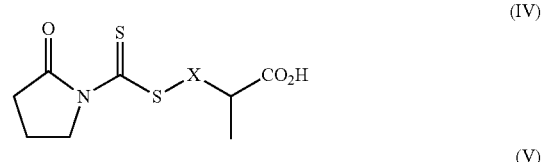

(IV)

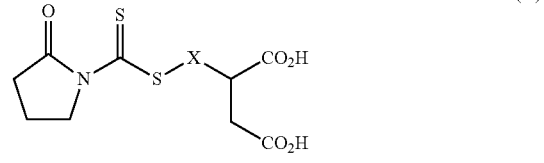

(V)

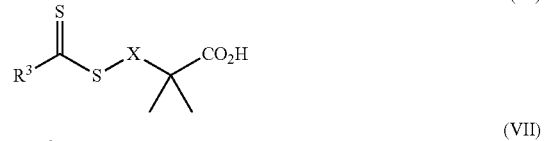

(VI)

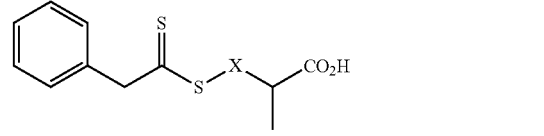

(VII)

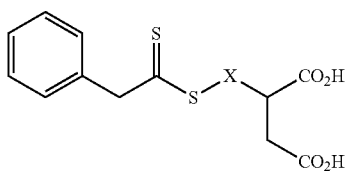
(VIII)

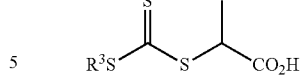
(XI)

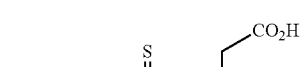
(XII)

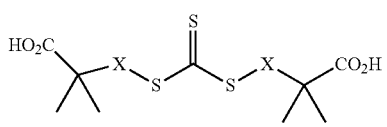
(IX)

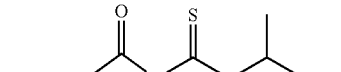
(XIII)

(XIV)

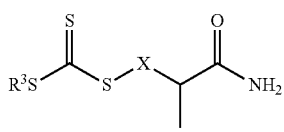
(X)

(XV)

where $R^3$ and X are as previously defined.

Preparing a steric stabiliser by RAFT polymerisation may involve polymerising under the control of a RAFT agent (i) one or more type of ethylenically unsaturated monomer to provide for at least one steric stabilising polymeric segment (A), and (ii) one or more type of different monomers to provide for at least one anchoring polymeric segment (B) (i.e. where A and B collectively form X in structure (I)). Techniques, conditions and reagents known by those skilled in the art of RAFT polymerisation may be conveniently used to prepare such stabilisers precursors.

Where the Z—C(S)—S— or $R^1$— moieties of general formula (I) are not particularly important with respect to providing the steric stabiliser used in accordance with the invention with its advantageous properties, one or both of these moieties (or part thereof) may be removed or modified using techniques known in the art. There are numerous techniques known to remove or modify at least the Z—C(S)—S— moiety or part thereof from RAFT derived polymers (e.g. the removal of the sulphur containing groups). For example, the RAFT derived polymer may be reacted with benzoyl peroxide.

Suitable RAFT agents for preparing steric stabilisers that may be used in accordance with the invention include, but are not limited to, those of general formula (IA):

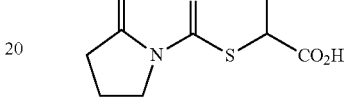
(XVI)

(XVII)

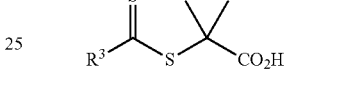
(XVIII)

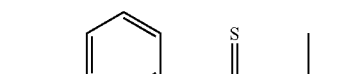
(IXX)

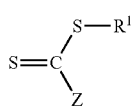
(IA)

where $R^1$ and Z are as previously defined.

In selecting both $R^1$ and Z groups for RAFT agents of the formula (IA), those agents resulting from the combination of preferred $R^1$ and Z groups are also preferred Preferred RAFT agents for preparing the steric stabilisers include, but are not limited to, those represented by the following general formulas (XI) to (IXX):

wherein $R^3$ is as previously defined.

When preparing a block copolymer structure of the steric stabiliser by any polymerisation technique, including RAFT polymerisation, those skilled in the art will also appreciate that each segment can be formed sequentially by the polymerisation of appropriate monomers. Alternatively, a preformed polymer may be employed as one of the segments and the other segment may be grafted thereto by the polymerisation of appropriate monomers.

Having regard to the discussion above concerning the required attributes of monomers that may be used to prepare the steric stabilising and anchoring polymeric segments, suitable monomers that may be used in general are those which can be polymerised by a free radical process. Suitable monomers should also be capable of being polymerised with other monomers. The factors which determine copolymerisability of various monomers are well documented in the art. For example, see: Greenlee, R. Z., in Polymer Handbook $3^{rd}$ Edition (Brandup, J., and Immergut. E. H. Eds) Wiley: New York, 1989 p II/53.

Such monomers, including those mentioned above, may be selected from those with the general formula (XX):

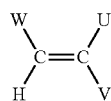

where U and W are independently selected from the group consisting of —CO$_2$H, —CO$_2$R$^1$, —COR$^1$, —CSR$^1$, —CSOR$^1$, —COSR$^1$, —CONH$_2$, —CONHR$^1$, —CONR$^1_2$, hydrogen, halogen and optionally substituted C$_1$-C$_4$ alkyl, or U and W form together a lactone, anhydride or imide ring that may itself be optionally substituted, wherein the substituents are independently selected from the group consisting of hydroxy, —CO$_2$H, —CO$_2$R$^1$, —COR$^1$, —CSR$^1$, —CSOR$^1$, —COSR$^1$, —CN, —CONH$_2$, —CONHR$^1$, —CONR$^1_2$, —OR$^1$, —SR$^1$, —O$_2$CR$^1$, —SCOR$^1$, and —OCSR$^1$; and V is selected from the group consisting of hydrogen, R$^2$, —CO$_2$H, —CO$_2$R$^2$, —COR$^2$, —CSR$^2$, —CSOR$^2$, —COSR$^2$, —CONH$_2$, —CONHR$^2$, —CONR$^2_2$, —OR$^2$, —SR$^2$, —O$_2$CR$^2$, —SCOR$^2$, and —OCSR$^2$;

where R$^2$ is selected from the group consisting of optionally substituted C$_1$-C$_{18}$ alkyl, optionally substituted C$_2$-C$_{18}$ alkenyl, optionally substituted aryl, optionally substituted heteroaryl, optionally substituted carbocyclyl, optionally substituted heterocyclyl, optionally substituted aralkyl, optionally substituted heteroarylalkyl, optionally substituted alkaryl, optionally substituted alkylheteroaryl and polymer chains wherein the substituents are independently selected from the group consisting of alkyleneoxidyl (epoxy), hydroxy, alkoxy, acyl, acyloxy, formyl, alkylcarbonyl, carboxy, sulfonic acid, alkoxy- or aryloxy-carbonyl, isocyanato, cyano, silyl, halo, amino, including salts and derivatives thereof. Preferred polymer chains include, but are not limited to, polyalkylene oxide, polyarylene ether and polyalkylene ether.

Examples of monomers of general formula (XX) include, but are not limited to, maleic anhydride, N-alkylmaleimide, N-arylmaleimide, dialkyl fumarate and cyclopolymerisable monomers, acrylate and methacrylate esters, acrylic and methacrylic acid, styrene, acrylamide, methacrylamide, and methacrylonitrile, mixtures of these monomers, and mixtures of these monomers with other monomers.

Further examples of monomers of general formula (XX) include the following: methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylamino styrene (all isomers), alpha-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropylacrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, ethylene and chloroprene. This list is not exhaustive.

When preparing a steric stabiliser for use in accordance with the invention by the polymerisation of ethylenically unsaturated monomers, the polymerisation may require initiation from a source of free radicals. The source of initiating radicals can be provided by any suitable method of generating free radicals, such as the thermally induced homolytic scission of suitable compound(s) (thermal initiators such as peroxides, peroxyesters, or azo compounds), the spontaneous generation from monomers (e.g. styrene), redox initiating systems, photochemical initiating systems or high energy radiation such as electron beam, X- or gamma-radiation. The initiating system is chosen such that under the reaction conditions there is no substantial adverse interaction between the initiator or the initiating radicals and other reagents present.

Thermal initiators are chosen to have an appropriate half life at the temperature of polymerisation. These initiators can include one or more of the following compounds:

2,2'-azobis(isobutyronitrile), 2,2'-azobis(2-cyanobutane), dimethyl 2,2'-azobis(isobutyrate), 4,4'-azobis(4-cyanovaleric acid), 1,1'-azobis(cyclohexanecarbonitrile), 2-(t-butylazo)-2-cyanopropane, 2,2'-azobis {2-methyl-N-[1,1-bis(hydroxymethyl)-2-hydroxyethyl]propionamide}, 2,2'-azobis[2-methyl-N-(2-hydroxyethyl)propionamide], 2,2'-azobis(N,N'-dimethyleneisobutyramidine)dihydrochloride, 2,2'-azobis(2-amidinopropane)dihydrochloride, 2,2'-azobis(N,N'-dimethyleneisobutyramidine), 2,2'-azobis{2-methyl-N-[1,1-bis(hydroxymethyl)-2-hydroxyethyl]propionamide}, 2,2'-azobis{2-methyl-N-[4,1-bis(hydroxymethyl)-2-ethyl]propionamide}, 2,2'-azobis[2-methyl-N-(2-hydroxyethyl)propionamide], 2,2'-azobis(isobutyramide)dihydrate, 2,2'-azobis(2,2,4-trimethylpentane), 2,2'-azobis(2-methylpropane), t-butyl peroxyacetate, t-butyl peroxybenzoate, t-butyl peroxyneodecanoate, t-butylperoxy isobutyrate, t-amyl peroxypivalate, t-butyl peroxypivalate, diisopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl hyponitrite, dicumyl hyponitrite. This list is not exhaustive.

Photochemical initiator systems are chosen to have the requisite solubility in the reaction medium and have an appropriate quantum yield for radical production under the conditions of the polymerisation. Examples include benzoin derivatives, benzophenone, acyl phosphine oxides, and photo-redox systems.

Redox initiator systems are chosen to have the requisite solubility in the reaction medium and have an appropriate rate of radical production under the conditions of the polymerisation; these initiating systems can include, but are not limited to, combinations of the following oxidants and reductants:

oxidants: potassium, peroxydisulfate, hydrogen peroxide, t-butyl hydroperoxide.

reductants: iron (II), titanium (III), potassium thiosulfite, potassium bisulfite.

Other suitable initiating systems are described in recent texts. See, for example, Moad and Solomon "the Chemistry of Free Radical Polymerisation", Pergamon, London, 1995, pp 53-95.

Suitable initiators which have an appreciable solubility in a hydrophilic reaction medium such as water include, but are not limited to, 4,4-azobis(cyanovaleric acid), 2,2'-azobis{2-methyl-N-[1,1-bis(hydroxymethyl)-2-hydroxyethyl]propionamide}, 2,2'-azobis[2-methyl-N-(2-hydroxyethyl)propionamide], 2,2'-azobis(N,N'-dimethyleneisobutyramidine), 2,2'-azobis(N,N'-dimethyleneisobutyramidine)dihydrochloride, 2,2'-azobis(2-amidinopropane)dihydrochloride, 2,2'-azobis{2-methyl-N-[1,1-bis(hydroxymethyl)-2-ethyl]propionamide}, 2,2'-azobis[2-methyl-N-(2-hydroxyethyl)propionamide], 2,2'-azobis(isobutyramide)dihydrate, and derivatives thereof.

Suitable initiators which have an appreciable solubility in a hydrophobic reaction medium may vary depending on the polarity of the reaction medium, but typically would include oil soluble initiators such as azo compounds exemplified by the well known material 2,2'-azobisisobutyronitrile. Other readily available initiators are acyl peroxides such as acetyl and benzoyl peroxide as well as alkyl peroxides such as cumyl and t-butyl peroxides. Hydroperoxides such as t-butyl and cumyl hydroperoxides may also be used.

Upon providing the dispersion as herein described, hydrophilic liquid is removed from the aqueous phase. Thus, water and any other hydrophilic solvents or liquids (if present) are removed from the aqueous phase. The function of this process is to force the nanomagnetic particles dispersed in the aqueous phase closer together so as to place the reactive functional groups of stabilisers anchored to a given particle in proximity for reaction with reactive functional groups of stabilisers anchored to neighbouring particles. Thus, it will only be necessary to remove sufficient hydrophilic liquid to achieve this. Generally, a majority of the hydrophilic liquid that forms the aqueous phase will be removed, for example at least 60 wt. %, or at least 70 wt. %, or at least 80 wt. %, or at least 90 wt. %, or at least 95 wt. %, or at least 99 wt. %.

Upon removal of hydrophilic liquid, it will be appreciated that the composition of the aqueous phase will in effect become concentrated. The concentrated "aqueous phase", which may now only contain little or no hydrophilic liquid, can advantageously remain dispersed throughout the continuous organic phase. The concentrated "aqueous phase" might therefore also be described as a dispersed phase comprising an aggregate of nanomagnetic particles having the steric stabiliser anchored thereto. Despite being in an "aggregated" form, it will be appreciated that each nanomagnetic particle within the aggregate will be separated from neighbouring particles by at least the polymeric chains of the steric stabilisers.

Provided that integrity of the dispersed aqueous phase is maintained, there is no particular limitation on the means by which hydrophilic liquid can be removed. For example, hydrophilic liquid may be removed by azeotropic distillation.

After removing sufficient hydrophilic liquid from the aqueous phase, reaction between the reactive functional groups of stabilisers may be promoted so as to form the polymeric matrix of the beads. Those skilled in the art will appreciate that the manner in which the reaction is promoted will vary depending on the type of reactive functional groups presented by the stabilisers. For example, the reaction between the functional groups may be thermally activated. In that case, the continuous organic phase may be heated so as to transfer heat to the dispersed phase comprising the aggregated nanomagnetic particles and thereby promote reaction of the functional groups of the steric stabilisers. Alternatively, provided that sufficient hydrophilic liquid has been removed, the dispersed phase may be separated from the continuous phase, for example by filtration, so as to provide precursor particles to the polymer microgel beads. The resulting isolated precursor particles may then be heated, for example by placing them in an oven, in order to promote reaction of the reactive functional groups and form the polymer microgel beads.

The mere removal of hydrophilic liquid from the aqueous phase per se may also be sufficient to promote reaction.

Thus, the steric stabiliser can in effect be covalently coupled to form the polymeric matrix of the beads.

The polymer content of the polymer microgel beads can be conveniently varied by increasing or decreasing the molecular weight of the steric stabilisers. Thus, an increase in the molecular weight of the stabilisers will increase the polymer content of the beads, whereas a decrease in the molecular weight of the stabilisers will decrease the polymer content of the beads, relative to a fixed nanomagnetic particle content.

The polymer content of the polymer microgel beads may also be varied by incorporating in the aqueous phase a polymer (hereinafter referred to as a polymeric modifier) having one or more functional groups that can react with the functional groups of the steric stabiliser. Thus, upon removing hydrophilic liquid from the aqueous phase, the polymeric modifier will remain and its functional groups can react so as to collectively with the steric stabilisers form the polymeric matrix of the beads.

Thus, the steric stabiliser can in effect be covalently coupled with one or more polymers other than the steric stabiliser to form the polymeric matrix of the beads.

Polymeric modifiers suitable for this purpose will be soluble in the aqueous phase and include, but are not limited to, polyacrylamide, polyethylene oxide, polyhydroxyethylacrylate, poly N-isopropylacrylamide, polydimethylaminoethylmethacrylate, polyvinyl pyrrolidone and copolymers thereof. Monomers that can be used to prepare such polymers are therefore acrylamide, ethylene oxide, hydroxyethylacrylate, N-isopropylacrylamide, dimethylaminoethylmethacrylate, vinyl pyrrolidone and combinations thereof.

The polymeric modifier will of course also present one or more reactive functional groups that can react with the reactive functional groups of the steric stabilisers. The polymeric modifier may therefore comprise one or more polymerised monomer residues that present the reactive functional group, or the polymeric modifier may be substituted with a reactive functional group post manufacture. In the latter case, the polymeric modifier will of course be prepared such that it can be readily substituted.

Generally, the polymeric modifier will be prepared such that it comprises one or more polymerised monomer residues that present the reactive functional group. The polymeric modifier will preferably comprise at least 2, at least 3, or at least 4 of such polymerised monomer residues. Monomers that may be used to present the reactive functional group in this regard include those described above for the steric stabiliser.

The crosslink density of the polymeric matrix of the beads may also be varied by increasing or decreasing the number of reactive functional groups provided by the steric stabiliser and/or the polymeric modifier (if present).

The polymer microgel beads in accordance with the invention may be used in various applications. It is believed that the beads are particularly suited for use in biomedical applications such as inducing hyperthermia in tissue. Hyperthermia has been proposed as a treatment of diseased tissue. There is evidence to suggest that hyperthermia is effective in treating diseases, including cancerous growths. The therapeutic benefit of hyperthermia therapy is believed to be mediated through two principle mechanisms. Firstly, hyperthermia therapy has a direct tumouricidal effect on tissue by raising temperatures to greater than about 41 or 42° C. resulting in irreversible damage to cancer cells. Secondly, hyperthermia is known to sensitise cancer cells to the effects of radiation therapy and to certain chemotherapeutic drugs.

In contrast to radiotherapy or chemotherapy, hyperthermia therapy is not prone to any cumulative toxicity effects.

The present invention therefore also provides a composition suitable for administration to a subject, the composition comprising polymer microgel beads in accordance with the invention and a pharmacologically acceptable carrier.

Compositions in accordance with the invention are suitable for administration to a subject. By the term "subject" is meant either an animal or human subject. By "animal" is meant primates, livestock animals (including cows, horses, sheep, pigs and goats), companion animals (including dogs, cats, rabbits and guinea pigs), and captive wild animals (including those commonly found in a zoo environment). Laboratory animals such as rabbits, mice, rats, guinea pigs and hamsters are also contemplated as they may provide a convenient test system. Preferably, the subject is a human subject.

By the composition being "suitable" for administration to a subject is meant that administration of the composition to a subject will not result in unacceptable toxicity, including allergenic responses and disease states.

By "administration" of the composition to a subject is meant that the composition is transferred to the subject. There is no particular limitation on the mode of administration, and the intended application will generally dictate the mode of administration. Generally, the compositions are administered in such a way as to cause the polymer microgel beads to concentrate in a target site. For example, the composition may be administered via intratumoral, peritumoral, or intravascular, intravenous, intraperitoneal, subcutaneous, intrahecal injection or superficial applications. The compositions in accordance with the invention are preferably administered via the arterial or venous blood supply.

The compositions in accordance with the invention comprise a pharmacologically acceptable carrier. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the polymer microgel beads are to be administered.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans.

Suitable pharmacologically acceptable carriers are described in Martin, Remington's Pharmaceutical Sciences, 18$^{th}$ Ed., Mack Publishing Co., Easton, Pa., (1990), and include, but are not limited to, liquids that may be sterilised such as water and oils, including those of petroleum, animal, vegetable or synthetic origin, such as peanut oil, soya bean oil, mineral oil, sesame oil, and the like. Water or soluble saline solutions and aqueous dextrose and glycerol solutions are preferably employed as carriers, particularly for injectable solutions.

The compositions in accordance with the invention may also include diluents of various buffer content (e.g. Tris-HCL, acetate, phosphate), pH and ionic strength; additives such as solubilising agents, anti-oxidants, and preservatives.

The compositions in accordance with the invention may be used to provide hyperthermic treatment of a target site in a subject.

As used herein, a "target site in a subject" is intended to mean a region of the subject that is considered to warrant hyperthermic treatment. There is no particular limitation regarding the location of the target site provided that the composition in accordance with the invention can be administered to it and that the target site can be exposed to the appropriate magnetic field. The target site will generally be diseased tissue, such as cancerous tissue.

A preferred use of compositions in accordance with the invention is to provide hyperthermic treatment of deep seated cancers such as liver cancer.

When used to heat subject tissue, the compositions in accordance with the invention preferably comprise polymer microgel beads of a size which ensures they are capable of being trapped in the capillary bed of the tissue (e.g. tumour) rather than being able to pass through the tissue into the venous supply. To effect this entrapment, the beads will preferably have a size ranging from about 10 microns to about 100 microns.

In order to promote the hyperthermic treatment, the target site is exposed to a magnetic field of clinically acceptable frequency and strength that causes the beads to radiate heat at the target site. By a magnetic field of a "clinically acceptable frequency and strength" is meant a magnetic field that will not result in unacceptable or undesirable physiological response in the subject being treated, be it from the magnetic field per se or its effect on the beads to radiate heat.

Generally, the magnetic field employed will be an alternating or AC magnetic field.

Upon being exposed to the magnetic field, the polymer microgel beads at the target site will generally exhibit a VAR of at least about 1 Watts/cm$^3$, more preferably at least about 10 Watts/cm$^3$, most preferably at least about 20 Watts/cm$^3$.

Generally, the beads at the target site will be exposed to an AC magnetic field with frequency in the range of about 50-300 kHz and strength of about 50-120 Oe, for example at a frequency of about 100 kHz and a strength of about 90 Oe.

Exposure of the target site to the appropriate magnetic field causes the polymer microgel beads at the site to heat, and this heat is conducted into the immediately surrounding site (e.g. diseased tissue). This method of heat treatment is generally known as Selectively Targeted Hyperthermia (STH).

It will be appreciated that adequate heating of the target site will be required for the hyperthermic treatment to be effective. Thus, the method for heating a target site in accordance with the invention provides a means to increase temperature in the target site to above 41° C. For use on the treatment of diseased tissue, the desired result is to decrease the viability of malignant cells. A decrease in the viability of malignant cells can result in either cell death or increased cell sensitivity to the effects of ionising radiation or chemotherapeutic drugs.

It is preferable that the method of heating a target site in accordance with the invention promotes heating of 42° C. at the target site for at least 30 minutes. The level of heating induced by the implanted polymer microgel beads will depend on several factors, including the VAR of the beads, the amount of material that can be localised in and around the target site, and the cooling factors in the environment of the polymer beads, such as blood perfusion.

The microgel beads may be administered in, as appropriate, a treatment or diagnostic effective amount. A treatment or diagnostic effective amount is intended to include an amount which, when administered according to the desired dosing regimen, achieves a desired therapeutic or diagnostic effect, including one or more of: alleviating the symptoms of, preventing or delaying the onset of, inhibiting or slowing the progression of, diagnosing, or halting or reversing altogether the onset or progression of a particular condition being treated and/or assessed.

Suitable dosage amounts and dosing regimens to achieve this can be determined by the attending physician and may depend on the particular condition being treated or diagnosed, the severity of the condition as well the general age, health and weight of the subject.

Compositions comprising the microgel beads may be administered in a single dose or a series of doses.

Where the compositions comprising the microgel beads are suitable for parenteral administration, they will generally be in the form of an aqueous or non-aqueous isotonic sterile injection solution that may contain one or more of an anti-oxidant, buffer, bactericide or solute which renders the composition isotonic with the blood of the intended subject. Such compositions may be presented in unit-dose or multi-dose sealed containers, for example, ampoules and vials.

In some applications it may be desirable to image the polymer microgel beads once they have been administered to a subject. The beads may therefore comprise a radioactive isotope for imaging purposes. Examples of suitable radioactive isotopes include $^{99m}$Tc, $^{67}$Ga, $^{64}$Cu, $^{89}$Zr and $^{18}$F. The beads may be radioactively labeled by any suitable means. For example, the isotope(s) may be conveniently combined with the nanomagnetic particles used in accordance with the invention.

The invention will now be described with reference to the following examples which illustrate some preferred embodiments of the invention. However, it is to be understood that the particularity of the following description is not to supersede the generality of the proceeding description of the invention.

Example 1

Preparation of a Poly(Acrylamide) Microgel Matrix Incorporating Iron Oxide Nanoparticles Part (a): Preparation of Diluted Aqueous Ferrofluid Stable in Acidic Medium Maghemite nanoparticles were produced following the method of Massart (*Preparation of aqueous magnetic liquids in alkaline and acidic media*. IEEE Transactions on Magnetics, 1981. MAG-17(2): p. 1247-1248). An aqueous mixture of ferric and ferrous chlorides was added to ammonia solution. The resulting precipitate was isolated by centrifugation then oxidized to maghemite by mixing with iron nitrate solution and heating. The precipitate was then washed in 2 molar nitric acid then finally peptised by water to form a dilute aqueous ferrofluid of approximately 5 wt % solids.

Part (b): Preparation of a poly(acrylic acid)$_{10}$-block-poly(acrylamide)$_{35}$-N-(isobutoxymethyl)acrylamide)$_3$ macro-RAFT agent using 2-{[butylsulfanyl) carbonothioyl]-sulfanyl}propanoic acid A solution of 2-{[butylsulfanyl)carbonothioyl]-sulfanyl}propanoic acid (0.46 g, 1.9 mmol), 4,4'-azobis(4-cyanovaleric acid) (0.03 g, 0.12 mmol), acrylamide (4.79 g, 67.4 mmol), N-(isobutoxymethyl)acrylamide (0.91 g, 5.8 mM) in dioxane (15 g) and water (7.6 g) was prepared in a 100 mL round bottom flask. This was stirred magnetically and sparged with nitrogen for 15 minutes. The flask was then heated at 70° C. for 2 hrs. At the end of this period, acrylic acid (1.39 g, 19.4 mmol) and 4,4'-azobis(4-cyanovaleric acid) (0.03 g, 0.12 mmol), were added to the flask. The mixture was deoxygenated and heating was continued at 70° C. for a further 3 hours. The copolymer solution had 32.8% solids. It was then diluted with MQ water to 0.6 wt %. The pH of the diluted copolymer solution was adjusted to 5 with 0.1M NaOH.

Part (c): Preparation of Sterically Stabilized Iron Oxide Nanoparticles from the Aqueous Ferrofluid of Part (a) and the Macro-Raft Agent of Part (b)

40 g of the nanoparticle dispersion (5 wt %) prepared in the part (a) was diluted with MQ water to 200 g to yield 1 wt % dispersion of the nanoparticles. The pH of this nanoparticle dispersion prepared was then raised to 5. A 100 g 0.6 wt % solution of the MacroRAFFT of copolymer also at pH 5 from part (b) was then added to a1 wt % dispersion of iron oxide maintained at the same pH. Mixture was vigorously stirred for 2 hours at room temperature. At this pH the copolymer is partially neutralized while the nanoparticles are sufficiently above their point of zero charge to also be stable. Carboxylate ions from the acrylic acid block of the copolymer chemically adsorbed onto the particle surface yielding a stable sterically stabilized dispersion of nanoparticles in water. The dispersion was then dialysed to remove salts, residual solvents, unwanted low molecular weight reaction side products and unbound polymer. The dialysed dispersion was sonicated for ten minutes at 30% amplitude using high energy sonic probe. The purified and sonicated nanoparticle dispersion was then distilled to increase the solid loading in the aqueous ferrofluid dispersion to about 55 wt %. The resulting aqueous ferrofluid was found to be stable in a 60% ammonium nitrate solution.

Part (d): Preparation of Poly(Acrylamide) Matrix Encapsulated Fe$_2$O$_3$ from the Water-Based Ferrofluid of Part (c)

1 g of the water based ferrofluid prepared in part (c) was taken in a 10 ml Scintillation vial. 100 g, 2 wt % solution of oil soluble surfactant, PIBSADEA in toluene was separately prepared in a 100 ml beaker. 2 g of this surfactant solution was then added to the scintillation vial containing ferrofluid. The mixture in scintillation vial emulsified on the vortex mixer for about 1 minute. The emulsion was then added to surfactant solution in 250 ml round bottom. The solution in round bottom flask was stirred mechanically. The flask was then heated slowly until the reflux temperature (110° C.) of toluene. Water from emulsion drops got stripped off along with toluene in the form of an azeotrope leaving dry microspheres in the continuous phase. Toluene was decanted form the mixture as microspheres precipitated under gravity. Microspheres were then washed couple of times with acetone to get rid of any left over toluene and also PIBSADEA surfactant. Microspheres at the end of this step are in dry powder form. Dry microspheres were then cured at 180° C. in heating oven for about 2 hour. This resulted in the crosslinking of polymer molecules stabilising the iron oxide nanoparticles within the microspheres. The beads had an average particle size of 35 microns as determined by light microscopy. When the resulting microgel beads were placed in an oscillating magnetic field of 100 kHz and 90 Oe they generated heat at a rate of 2.9 W/g.

Example 2

Preparation of a Poly(Acrylamide) Microgel Matrix Incorporating Iron Oxide Nanoparticles Part (a): Preparation of Diluted Aqueous Ferrofluid Stable in Acidic Medium Maghemite nanoparticles were produced following the method of Massart (*Preparation of aqueous magnetic liquids in alkaline and acidic media*. IEEE Transactions on Magnetics, 1981. MAG-17(2): p. 1247-1248). An aqueous mixture of ferric and ferrous chlorides was mixed with an ammonia solution. The resulting precipitate was isolated by magnetic sedimentation then oxidized to maghemite by mixing with iron nitrate solution and heating. The precipitate was then washed in 2 molar nitric acid and acetone. The precipitate was peptised by water to form a dilute aqueous ferrofluid of approximately 13 wt % solids and a particle size of approximately 3-20 nm in diameter was determined by transmission electron microscope (TEM).

Part (b): Preparation of a poly(acrylic acid)$_{10}$-block-poly(acrylamide)$_{20}$-N-(isobutoxymethyl)acrylamide)$_3$ macro-RAFT agent using 2-{[dodecylsulfanyl)carbonothioyl]-sulfanyl}propanoic acid A solution of 2-{[dodecylsulfanyl)carbonothioyl]-sulfanyl}propanoic acid (2.11 g, 6.0 mmol), 4,4'-azobis(4-cyanovaleric acid) (0.09 g, 0.31 mmol), acrylamide (8.55 g, 120.3 mmol), N-(isobutoxymethyl)acrylamide (2.75 g, 17.5 mM) in dioxane (30 g) and water (15 g) was prepared in a 250 ml round bottom flask. This was stirred magnetically and sparged with nitrogen for 15 minutes. The flask was then heated at 70° C. for 3 hours. At the end of this period, acrylic acid (4.58 g, 63.5 mmol) and 4,4'-azobis(4-cyanovaleric acid) (0.09 g, 0.31 mmol), were added to the flask. The mixture was deoxygenated and heating was continued at 70° C. for a further 3 hours. The copolymer solution had 31.6% solids. It was then diluted with MQ water to 0.6 wt %. The pH of the diluted copolymer solution was adjusted to 5 with 0.1 M NaOH.

Part (c): Preparation of Sterically Stabilized Iron Oxide Nanoparticles from the Aqueous Ferrofluid of Part (a) and the Macro-Raft Agent of Part (b)

42 g of the nanoparticle dispersion (13 wt %) prepared in the part (a) was diluted with MQ water to 550 g to yield 1 wt % dispersion of the nanoparticles. The pH of this nanoparticle dispersion prepared was then raised to 5. A 500 g 0.6 wt % solution of the macro-RAFT also at pH 5 from Example 2, part (b) was then mixed with a 1 wt % dispersion of iron oxide maintained at the same pH. Mixture was vigorously stirred for 2 hours at room temperature. At this pH the copolymer is partially neutralized while the nanoparticles are sufficiently above their point of zero charge to also be stable. Carboxylate ions from the acrylic acid block of the copolymer chemically adsorbed onto the particle surface yielding a stable sterically stabilized dispersion of nanoparticles in water. The dispersion was then dialysed to remove salts, residual solvents, unwanted low molecular weight reaction side products and unbound polymer. The dialysed dispersion was sonicated for thirty minutes at 50% amplitude using high energy sonic probe. The purified and sonicated nanoparticle dispersion was then distilled to increase the solid loading in the aqueous ferrofluid dispersion to about 40 wt %. The resulting aqueous ferrofluid was found to be stable in concentrated sodium chloride solution and standard phosphate buffered saline.

Part (d): Preparation of Poly(Acrylamide) Matrix Encapsulated Fe$_2$O$_3$ from the Water-Based Ferrofluid of Part (c)

14 g of the water based ferrofluid prepared in part (c) was taken in a 500 ml glass jar. 710 g, 4.8 wt % solution of oil soluble surfactant, PIBSADEA in toluene was separately prepared in a 1 l round bottom flask. 160 g of this surfactant solution was then added to the jar containing ferrofluid. The mixture in the glass jar emulsified for ten minutes in a sonication bath and sonicated for five minutes at 30% amplitude until almost translucent. The emulsion was then added to surfactant solution in 2 l round bottom flask. The solution in round bottom flask was stirred mechanically. The flask was then heated slowly until the reflux temperature (110° C.) of toluene. Water from emulsion drops got stripped off along with toluene in the form of an azeotrope leaving dry microspheres in the continuous phase. Toluene was decanted form the mixture as microspheres precipitated over a magnet. Microspheres were then washed couple of times with toluene to get rid of any left over PIBSADEA surfactant. Microspheres are dried about 2 of hours at 60° C. and at the end of this step are in dry powder form. Dry microspheres were then cured at 180° C. in heating oven for about 5 hours. This resulted in the crosslinking of polymer molecules, stabilising iron oxide nanoparticles within the microspheres. The particle size of the beads was determined by TEM and found to be in the range of 400-700 nm in diameter.

The invention claimed is:

1. Polymer microgel beads (a) having a polymeric matrix that can absorb and be swollen by an aqueous liquid, and (b) incorporating nanomagnetic particles, wherein a steric stabiliser is associated with the particles which are distributed substantially uniformly throughout the polymeric matrix, the steric stabiliser being a polymeric material that (i) forms at least part of the polymeric matrix of the beads, and (ii) comprises a steric stabilising polymeric segment and an anchoring polymeric segment, wherein the steric stabilising polymeric segment is soluble in an aqueous liquid and differs from the anchoring polymeric segment, and wherein the anchoring polymeric segment has an affinity toward the surface of the nanomagnetic particles and binds the stabiliser to the particles.

2. The polymer microgel beads according to claim 1, wherein the beads have a size ranging from about 10 microns to about 50 microns.

3. The polymer microgel beads according to claim 1, wherein nanomagnetic particles have a size of less than 50 nm.

4. The polymer microgel beads according to claim 1, wherein nanomagnetic particles are present in at amount of at least 30 wt. %.

5. The polymer microgel beads according to claim 1, wherein nanomagnetic particles are selected from iron, nickel, chromium, cobalt, oxides thereof and combinations thereof.

6. The polymer microgel beads according to claim 1, wherein nanomagnetic particles are selected from magnetite ($Fe_3O_4$), maghemite ($\gamma\text{-}Fe_2O_3$) and combinations thereof.

7. The polymer microgel beads according to claim 1, wherein the polymeric matrix of the beads is formed from covalently coupled steric stabiliser.

8. The polymer microgel beads according claim 1, wherein the polymeric matrix of the beads is formed from steric stabiliser is covalently coupled with one or more polymers other than steric stabiliser.

9. The polymer microgel beads according to claim 7, wherein the steric stabiliser is covalently coupled through a reaction residue of one or more functional groups selected from acetoacetoxyethyl methacrylate, glycidyl methacrylate, N-methylolacrylamide, (isobutoxymethyl)acrylamide, hydroxyethyl acrylate, t-butyl-carbodiimidoethyl methacrylate, acrylic acid, γ-methacryloxypropyltriisopropoxysilane, 2-isocyanoethyl methacrylate and diacetone acrylamide.

10. The polymer microgel beads according to claim 1, wherein the steric stabiliser has a number average molecular weight ranging from about 1,000 to about 3,000.

11. The polymer microgel beads according to claim 1, wherein at least one of the steric stabilising polymeric segment and the anchoring polymeric segment is derived from one or more ethylenically unsaturated monomers that have been polymerised by living polymerisation.

12. The polymer microgel beads according to claim 1, wherein the steric stabilising polymeric segment comprises polyacrylamide, polyethylene oxide, polyhydroxyethylacrylate, poly N-isopropylacrylamide, polydimethylamino ethylmethacrylate, polyvinyl pyrrolidone or a copolymer thereof.

13. The polymer microgel beads according to claim 1, wherein the anchoring polymeric segment comprises polyacrylic acid, polymethacrylic acid, polystyrene, polyitaconic acid, poly-p-styrene carboxylic acids, poly-p-styrene sulfonic acids, polyvinyl sulfonic acid, polyvinyl phosphonic acid, poly monoacryloxyethyl phosphate, poly-2-(methylacryloyloxy) ethyl phosphate, polyethacrylic acid, poly-alpha-chloroacrylic acid, polycrotonic acid, polyfumaric acid, polycitraconic acid, polymesaconic acid, polymaleic acid, poly-2-(dimethyl amino) ethyl and propyl acrylates and methacrylates, poly-3-(diethyl amino) ethyl and propyl acrylates and methacrylates, polydimethylaminoethyl-methacrylate, or a copolymer thereof.

14. The polymer microgel beads according to claim 1, wherein the anchoring polymeric segment comprises at least 5 polymerised monomer residues that each provide a site that functions to secure the stabiliser to the particles.

15. The polymer microgel beads according claim 1 further comprising one or more radioactive isotopes.

16. A method of preparing polymer microgel beads incorporating nanomagnetic particles, the method comprising:
(i) providing a dispersion comprising a continuous organic phase and a dispersed aqueous phase, the dispersed aqueous phase comprising hydrophilic liquid and nanomagnetic particles dispersed throughout the aqueous phase, the nanomagnetic particles being maintained in their dispersed state by a steric stabiliser, wherein the steric stabiliser is a polymeric material comprising:
(a) a steric stabilising polymeric segment and an anchoring polymeric segment, wherein the steric stabilising polymeric segment is soluble in the aqueous phase and differs from the anchoring polymeric segment, and wherein the anchoring polymeric segment has an affinity toward the nanomagnetic particles and secures the steric stabiliser to the particles; and
(b) one or more reactive functional group;
(ii) removing hydrophilic liquid from the aqueous phase; and
(iii) promoting a reaction between the reactive functional groups of the steric stabilisers to thereby form the polymer microgel beads incorporating the nanomagnetic particles.

17. A composition suitable for administration to a subject, the composition comprising a pharmacologically acceptable carrier and polymer microgel beads in accordance with claim 1.

18. A composition in accordance with claim 17 in the form of an aqueous or nonaqueous sterile injectable solution which optionally contains one or more of an antioxidant, buffer, bactericide or solute which renders the composition isotonic with the blood of the intended subject.

19. A method for heating a target site of interest in a subject, the method comprising:
(i) administering a composition according to claim 17 to the subject; and
(ii) exposing at least the target site of interest to a magnetic field of a clinically acceptable frequency and strength such that the microgel beads from the composition radiate heat at the target site.

20. A method of performing hyperthermia therapy on a target site of interest in a subject, the method comprising administering a composition according to claim 17 to the subject and exposing at least the target site to a magnetic field of clinically acceptable frequency and strength to promote the hyperthermia therapy.

21. The method according to claim 20, wherein the target site of interest is cancerous tissue.

22. The method according to claim 19, wherein after administering the composition to the subject and exposing at least the target site to the magnetic field, the polymer microgel beads at the target site exhibit a volumetric absorption rate (VAR) of at least 1 Watts/$cm^3$.

23. The process of using a composition according to claim 18 in a method of performing hyperthermia therapy.

* * * * *